(12) United States Patent
Skafidas et al.

(10) Patent No.: US 11,690,566 B2
(45) Date of Patent: Jul. 4, 2023

(54) SALIVA TESTING SYSTEM

(71) Applicant: MX3 Diagnostics, Inc., Austin, TX (US)

(72) Inventors: Efstratios Skafidas, Thornbury (AU); Chathurika Darshani Abeyrathne, Mitcham (AU); Gursharan Chana, Carlton (AU); Duc Hau Huynh, Lalor (AU); Trevor John Kilpatrick, Parkville (AU); Alan D. Luther, Edina, MN (US); Michael Luther, Austin, TX (US); Phuong Duc Nguyen, Albion (AU); Thanh Cong Nguyen, Sunshine West (AU)

(73) Assignee: MX3 Diagnostics, Inc., Austin, TX (US)

( * ) Notice: Subject to any disclaimer, the term of this patent is extended or adjusted under 35 U.S.C. 154(b) by 728 days.

(21) Appl. No.: 16/197,530

(22) Filed: Nov. 21, 2018

(65) Prior Publication Data

US 2019/0150836 A1    May 23, 2019

Related U.S. Application Data

(60) Provisional application No. 62/589,028, filed on Nov. 21, 2017.

(51) Int. Cl.
*A61B 5/00*    (2006.01)
*A61B 10/00*    (2006.01)
(Continued)

(52) U.S. Cl.
CPC .......... *A61B 5/4875* (2013.01); *A61B 5/0002* (2013.01); *A61B 5/14507* (2013.01);
(Continued)

(58) Field of Classification Search
CPC .............. A61B 5/4875; A61B 5/14546; A61B 10/0051; A61B 5/14507;
(Continued)

(56) References Cited

U.S. PATENT DOCUMENTS 4,454,007 A    6/1984  Pace
5,714,341 A *  2/1998  Thieme .............. G01N 33/5302
                                                    435/22
(Continued)

FOREIGN PATENT DOCUMENTS

CN    109682878 A    4/2019
EP    1710565       10/2006
(Continued)

OTHER PUBLICATIONS

Oncescu et al., "Smartphone based health accessory for colorimetric detection of biomarkers in sweat and saliva," Lab on a Chip 13(16):13232-3238, Jun. 7, 2013.
(Continued)

*Primary Examiner* — May A Abouelela
(74) *Attorney, Agent, or Firm* — Knobbe, Martens, Olson & Bear LLP

(57) ABSTRACT

A method for using saliva to measure at least one substance or physiological parameter of a human or animal subject may involve inserting a first end of a sensor into a handheld saliva testing device. The method may also involve receiving saliva from the subject on a second end of the sensor, moving the saliva from the second end of the sensor to the first end, and processing the saliva with the handheld saliva testing device to provide initial saliva data related to the at least one substance or physiological parameter of the subject. In some embodiments, the sensor remains inserted in the handheld device while the subject deposits saliva on the opposite, free end of the sensor.

18 Claims, 24 Drawing Sheets

(51) Int. Cl.
*A61B 5/145* (2006.01)
*G01N 33/487* (2006.01)
*G01N 33/50* (2006.01)
*C12Q 1/00* (2006.01)

(52) U.S. Cl.
CPC ........ *A61B 5/14546* (2013.01); *A61B 5/6898* (2013.01); *A61B 10/0051* (2013.01); *C12Q 1/001* (2013.01); *G01N 33/48785* (2013.01); *G01N 33/50* (2013.01); *A61B 2010/0003* (2013.01); *G01N 33/487* (2013.01)

(58) Field of Classification Search
CPC .......... A61B 2010/0003; A61B 5/0002; A61B 5/6898; C12Q 1/001; G01N 33/487; G01N 33/48785; G01N 33/50
USPC ....................................................... 600/584
See application file for complete search history.

(56) References Cited

U.S. PATENT DOCUMENTS

| | | | |
|---|---|---|---|
| 6,102,872 A * | 8/2000 | Doneen | A61B 5/14532 422/50 |
| 6,554,982 B1 | 4/2003 | Shin et al. | |
| 9,546,973 B2 * | 1/2017 | McIlrath | G01N 27/3274 |
| 10,197,523 B2 * | 2/2019 | Huang | G01N 27/3272 |
| 10,258,278 B2 * | 4/2019 | Howell | A61B 5/4277 |
| 10,989,724 B1 * | 4/2021 | Holmes | G01N 35/02 |
| 2001/0032785 A1 | 10/2001 | Cha et al. | |
| 2002/0011408 A1 | 1/2002 | Lee et al. | |
| 2002/0060247 A1 | 5/2002 | Krishnaswamy et al. | |
| 2002/0065332 A1 | 5/2002 | Choi et al. | |
| 2003/0150745 A1 | 8/2003 | Teodorczyk et al. | |
| 2003/0171697 A1 * | 9/2003 | Smith | B01L 3/5023 600/584 |
| 2004/0238358 A1 | 12/2004 | Forrow et al. | |
| 2005/0143675 A1 | 6/2005 | Neel et al. | |
| 2005/0279647 A1 | 12/2005 | Beaty | |
| 2006/0137980 A1 | 6/2006 | Lauks et al. | |
| 2007/0015287 A1 * | 1/2007 | Robbins | G01N 33/84 436/164 |
| 2007/0048224 A1 * | 3/2007 | Howell | A61B 10/0051 424/9.1 |
| 2007/0073127 A1 | 3/2007 | Kiani et al. | |
| 2007/0098600 A1 | 5/2007 | Kayyem | |
| 2007/0272564 A1 | 11/2007 | Huang | |
| 2008/0118397 A1 | 5/2008 | Slowey et al. | |
| 2009/0024060 A1 * | 1/2009 | Darrigrand | A61B 10/0051 600/584 |
| 2010/0176006 A1 | 7/2010 | Bickford et al. | |
| 2010/0249652 A1 | 9/2010 | Rush et al. | |
| 2012/0067741 A1 | 3/2012 | Kranendonk et al. | |
| 2012/0083711 A1 * | 4/2012 | Goldstein | A61B 5/4875 600/573 |
| 2012/0109011 A1 * | 5/2012 | Cogan | A61B 10/0051 600/584 |
| 2012/0165626 A1 | 6/2012 | Irina et al. | |
| 2013/0199944 A1 | 8/2013 | Petisee | |
| 2013/0233061 A1 | 9/2013 | Sullivan | |
| 2013/0341186 A1 | 12/2013 | Hsu | |
| 2014/0277291 A1 * | 9/2014 | Pugh | G02C 7/04 607/88 |
| 2014/0326037 A1 | 11/2014 | Fukuda et al. | |
| 2015/0091592 A1 | 4/2015 | Elder | |
| 2015/0216471 A1 * | 8/2015 | Goldstein | A61B 5/4848 600/373 |
| 2015/0217115 A1 * | 8/2015 | Avitall | A61B 5/14507 607/58 |
| 2015/0226695 A1 | 8/2015 | Bakker et al. | |
| 2015/0226752 A1 | 8/2015 | Nazareth et al. | |
| 2015/0359458 A1 * | 12/2015 | Erickson | G16Z 99/00 455/557 |
| 2016/0011178 A1 | 1/2016 | Hoenes et al. | |
| 2016/0120468 A1 * | 5/2016 | Mathew | A61B 5/01 600/301 |
| 2016/0266102 A1 | 9/2016 | Knopfmacher | |
| 2016/0320326 A1 | 11/2016 | Zevenbergen | |
| 2016/0361001 A1 * | 12/2016 | Tai | A61B 5/7246 |
| 2017/0014822 A1 | 1/2017 | Ker | |
| 2017/0027506 A1 * | 2/2017 | Howell | G01N 21/81 |
| 2017/0138962 A1 * | 5/2017 | Southern | A61B 10/00 |
| 2017/0261461 A1 | 9/2017 | Bychkova et al. | |
| 2018/0125400 A1 * | 5/2018 | Yang | A61B 5/1486 |
| 2018/0220947 A1 * | 8/2018 | Bedell, Jr. | A61B 5/02416 |
| 2020/0011851 A1 | 1/2020 | Piasio et al. | |
| 2020/0116664 A1 | 4/2020 | Abeyrathne et al. | |
| 2020/0383582 A1 * | 12/2020 | Bychkov | G16H 50/30 |
| 2021/0005233 A1 | 1/2021 | Kim et al. | |
| 2021/0005322 A1 | 1/2021 | Huynh et al. | |
| 2021/0007646 A1 | 1/2021 | Nguyen et al. | |
| 2021/0215662 A1 | 7/2021 | Erlichster et al. | |
| 2021/0223239 A1 * | 7/2021 | de Haan | G01N 33/54387 |
| 2021/0239586 A1 | 8/2021 | Skafidas et al. | |
| 2022/0013212 A1 * | 1/2022 | Tseng | G01L 1/16 |
| 2022/0122743 A1 | 4/2022 | Erlichster et al. | |
| 2022/0143609 A1 | 5/2022 | Xu et al. | |

FOREIGN PATENT DOCUMENTS

| | | |
|---|---|---|
| EP | 2075339 A1 | 7/2009 |
| KR | 20160035584 A | 3/2016 |
| WO | WO2010045247 A1 | 4/2010 |
| WO | WO2011075711 A1 | 6/2011 |
| WO | WO2014176753 | 11/2014 |

OTHER PUBLICATIONS

Partial International Search in Application No. PCT/US2018/062243, dated Feb. 11, 2019, 12 pages.

International Search Report and Written Opinion for PCT Application No. PCT/US2018/062243, dated Apr. 3, 2019, 17 pages.

"Cepheid and Sherlock Biosciences Establish Collaboration on New GeneXpert Tests for Infectious Diseases and Oncology Leveraging CRISPR Technology, http://cepheid.mediaroom.com/2020-02-28-Cepheid-and-Sherlock-Biosciences-Establish-Collaboration-on-New-GeneXpert-Tests-for-Infectious-Diseases-and-Oncology-Leveraging-CRISPR-Technology, 3 pages (Feb. 28, 2020)."

"Cepheid, Xpert Carba-R, GXCARBAR-10, https://www.cepheid.com/Package%20Insert20Files/Xpert-Carba-R-RX-Only-US-IVD-ENGLISH-Package-Insert-301-2438-Rev-F.pdf, Rev. F, 54 pages (Aug. 2019)."

A. Moya, et al., "Flexible Microfluidic Bio-Lab-on-a-Chip Multi-Sensor Platform for Electrochemical Measurements", Sensors, 2014 IEEE, pp. 1018-1021 (Year: 2014).

Erlichster et al., "Assessment of Biomarker Concentration in a Fluid," U.S. Appl. No. 62/961,438, filed Jan. 15, 2020, 22 pages.

Erlichster et al., "Pan-Family Assays for Rapid Viral Screening: Reducing Delays in Public Health Responses During Pandemics", Clinical Infectious Diseases, Jul. 20, 2020 (Jul. 20, 2020), pp. 1-6, XP055830068.

Erlichster et al., "Personalized Hydration Assessment and Fluid Replenishment," U.S. Appl. No. 62/876,263, filed Jul. 19, 2019, 30 pages.

Erlichster et al., "Personalized Hydration Assessment and Fluid Replenishment," U.S. Appl. No. 62/957,527, filed Jan. 6, 2020, 35 pages.

International Preliminary Report on Patentability and Written Opinion, re PCT Application No. PCT/US2018/062243, dated Jun. 4, 2020.

Nguyen et al., "Saliva Test Strip and Method" U.S. Appl. No. 62/872,339, filed Jul. 10, 2019, 31 pages.

Paul K et al., "The arrival of a true point-of-care molecular assay-ready for global implementation?", Nov. 1, 2015 (Nov. 1, 2015), pp. e663-e664, XP055830065.

(56) References Cited

OTHER PUBLICATIONS

Skafidas et al., "Biological Fluid Sample Assessment," U.S. Appl. No. 62/967,694, filed Jan. 30, 2020, 21 pages.

* cited by examiner

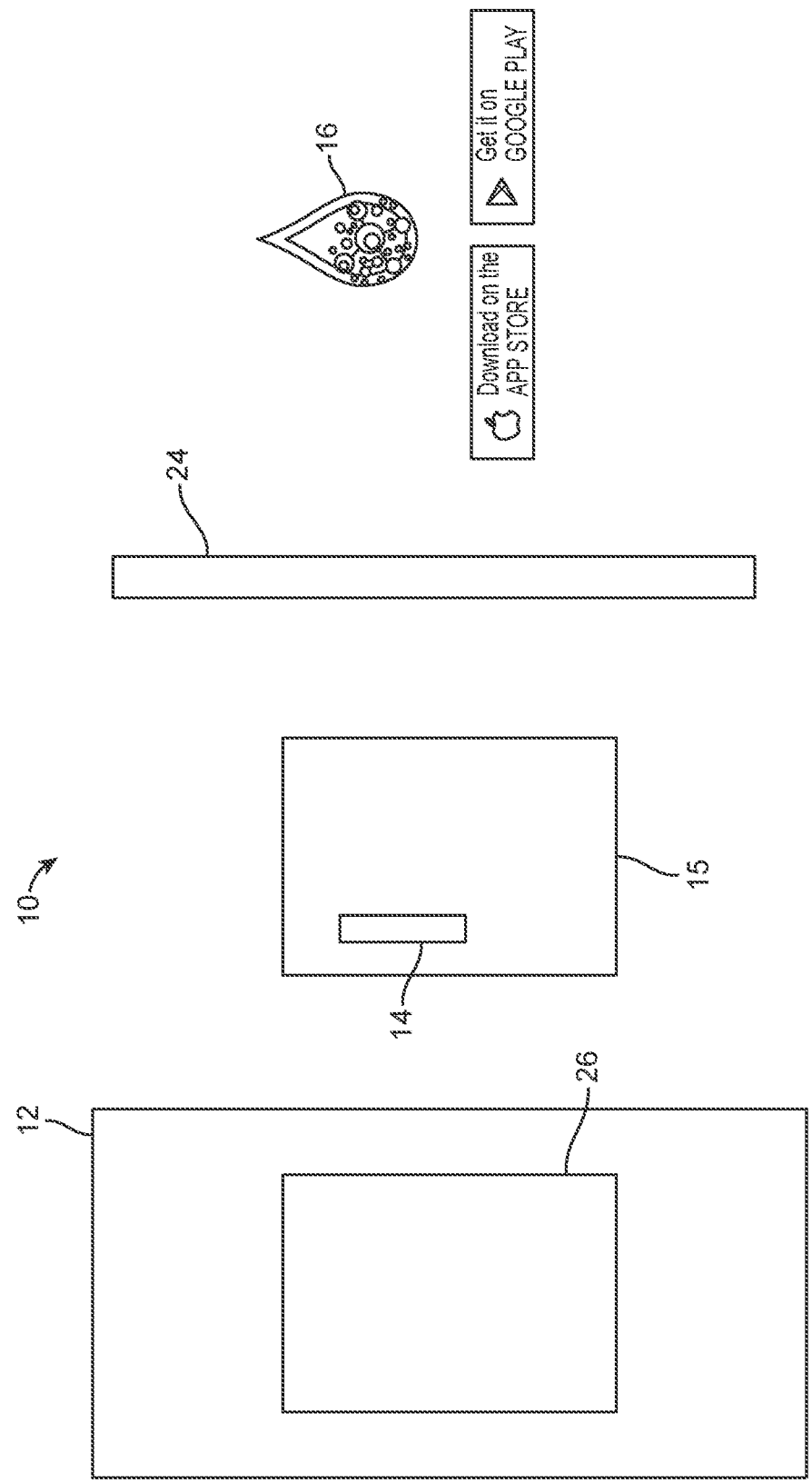

SALIVA TESTING SYSTEM

CROSS-REFERENCE TO RELATED APPLICATIONS

This application claims the benefit of U.S. Provisional Patent Application No. 62/589,028, filed Nov. 21, 2017, entitled, "SALIVA TESTING SYSTEM." The disclosure of this priority application is hereby incorporated by reference in its entirety into the present application.

TECHNICAL FIELD

This application is directed to medical devices, systems and methods. More specifically, the application is directed to devices, systems and methods that use saliva to measure one or more physiological parameters.

BACKGROUND OF THE INVENTION

Appropriate hydration in the human body is vital for health and proper functioning of the body organs. Water is lost from the body during respiration, perspiration and urination. Fluid loss of just a few percent can negatively impact cardiovascular function, thermal dissipation, and exercise performance. Dehydration can cause headaches, light-headedness, dizziness, fainting and in extreme cases delirium, unconsciousness or death. Hyponatremia ("over-hydration") can also detrimentally affect the body's functioning, particularly during exercising, and can even lead to death in extreme cases.

Dehydration is considered an excessive loss of body fluid. In physiological terms, dehydration may entail a deficiency of fluid within an organism. Dehydration may be caused by losing too much fluid, not drinking enough water or fluids, or both. Vomiting, diarrhea, and excessive perspiration without sufficient liquid intake are other causes of dehydration, which may be particularly worrisome for athletes and people that work under hot and dry conditions. There are three main types of dehydration: hypotonic (primarily a loss of electrolytes, especially sodium), hypertonic (primarily a loss of water), and isotonic (equal loss of water and electrolytes). While isotonic dehydration is the most common, distinction between the three types of dehydration may be important for administering proper treatment.

Relying on thirst as a feedback mechanism to trigger demand for fluid intake may not be adequate to maintain an optimal hydration level, since a sensation of thirst sufficient to cause a subject to drink is often not triggered until after the subject is already dehydrated. Unfortunately, there are currently no practical, affordable, non-invasive devices for measuring a person's hydration level. Measurement devices that use blood or urine to measure hydration are impractical, invasive, expensive or some combination thereof.

There are many other physiological parameters and levels of various substances in the human or animal body that are frequently tested or would be desirable to test for. Unfortunately, it is often necessary to sample blood, urine or other substances, such as cerebrospinal fluid, to measure a desired parameter. Or, even worse, some parameters may involve even more invasive or costly tests.

Therefore, it would be highly beneficial to have a practical, affordable, non-invasive system and method for measuring a person's hydration level. It would also be very desirable to have practical, affordable, non-invasive systems and methods for testing other parameters in the body.

BRIEF SUMMARY

Saliva may be an ideal bodily substance for use in measuring hydration and dehydration. Saliva is easily obtained with minimal invasiveness, but it is a complex fluid. Approximately 99% of saliva is water, and the remaining 1% consists of large organic molecules, such as proteins, small organic molecules, such as urea, and electrolytes, such as sodium and potassium. Whole saliva, considered as the total fluid content of the mouth, contains many other constituents, including serum components, blood cells, bacteria, bacterial products, epithelial cells, cell products, food debris and bronchial secretions. Thus, processing saliva to measure an individual's hydration level is challenging but likely highly beneficial if done effectively.

The present application describes systems, methods and devices for testing (or "measuring" or "analyzing") saliva, to measure a subject's hydration level. These same systems, methods and devices, or variations thereof, may also be used to measure one or more other substances and/or physiological parameters in a human or animal subject. The details of these systems, methods and devices are described in further detail below.

In one aspect of the present disclosure, a method for using saliva to measure at least one substance or physiological parameter of a human or animal subject involves: inserting a first end of a sensor into a handheld saliva testing device; receiving saliva from the subject on a second end of the sensor; moving the saliva from the second end of the sensor to the first end; and processing the saliva with the handheld saliva testing device to provide initial saliva data related to the at least one substance or physiological parameter of the subject. In some cases, the saliva is received on the second end of the sensor while the first end of the sensor remains inserted within the handheld saliva testing device. For example, receiving the saliva may involve simply contacting the second end of the sensor with the subject's tongue, lips or mouth. In some embodiments, the method may also include: providing an audio and/or visual alert with the handheld saliva testing device when a sufficient amount of saliva is received on the sensor; and removing the second end of the sensor from the subject's tongue or mouth. Typically, the saliva is automatically processed with the processor after the alert is provided.

The method may further involve transmitting the initial saliva data from the handheld saliva testing device to a computer processor and processing the initial saliva data with the computer processor to provide final measurement data describing the at least one substance or physiological parameter. In some embodiments, the initial saliva data is transmitted wirelessly to the computer processor, which is located separately from the handheld saliva measurement device. For example, the computer processor may be an application on a mobile computing device. In some embodiments, the measured parameter is hydration, and the final measurement data includes a hydration score for the subject. Other examples of the substance or physiological parameter that may be measured include, but are not limited to, lactate level, ketones, glucose, glycerides, sodium, potassium, calcium, magnesium, chlorides, phosphates, caffeine, melatonin, c-reactive protein, chemokines, cytokines, troponin, cortisol, creatinine kinase, insulin, beta hydroxyl butyrate, iron, ferritin, salivary amylase and oxalic acid.

Moving the saliva involves moving the saliva through at least one microfluidic channel in the sensor. Optionally, moving the saliva may also involve moving the saliva through a chemically functionalized mesh embedded in the sensor. The method may also include ejecting the sensor from the handheld saliva testing device, by pressing an eject button the handheld saliva testing device, after the saliva has been analyzed.

In another aspect of the present application, a method for using saliva to measure at least one substance or physiological parameter of a human or animal subject may involve: inserting a first end of a sensor into a handheld saliva testing device; contacting a second end of the sensor with the subject's tongue or mouth to collect the subject's saliva on the second end of the sensor; moving the saliva from the second end of the sensor to the first end; analyzing the saliva with the handheld saliva testing device to determine if there is a sufficient amount of the saliva to provide a measurement; providing an audio and/or visual alert with the handheld saliva testing device when the sufficient amount of saliva is received on the sensor; and analyzing the saliva with the handheld saliva testing device to measure the substance or physiological parameter.

In another aspect of the present disclosure, a system for testing saliva to measure at least one substance or physiological parameter of a human or animal subject may include: a handheld saliva testing device comprising a sensor slot and a display; a sensor comprising a first end configured for insertion into the sensor slot of the handheld saliva testing device and a second end configured for receiving saliva directly from the subject's mouth; and a computer processor coupled with the handheld saliva testing device to process initial data from the handheld saliva testing device to provide final measurement data describing the at least one substance or physiological parameter.

In some embodiments, the sensor is configured to receive the saliva on the second end of the sensor while the first end of the sensor remains inserted within the handheld saliva testing device. The computer processor may be located separately from, and may be wirelessly connectable to, the handheld saliva measurement device. In some embodiments, the computer processor is an application on a mobile computing device. In some embodiments, the parameter is hydration, and the computer processor is configured to generate the final measurement data, including a hydration score for the subject. In various other embodiments, the substance or physiological parameter may include, but is not limited to, lactate level, ketones, glucose, glycerides, sodium, potassium, calcium, magnesium, chlorides, phosphates, caffeine, melatonin, c-reactive protein, chemokines, cytokines, troponin, cortisol, creatinine kinase, insulin, beta hydroxyl butyrate, iron, ferritin, salivary amylase and oxalic acid.

The sensor may include at least one microfluidic channel for directing saliva from the second end to the first end of the sensor and a chemically functionalized mesh embedded between a top layer and a bottom layer of the sensor, to facilitate movement of saliva along a length of the sensor. The system may include an additional computer processor embedded in the handheld saliva testing device for generating the initial data. The handheld saliva testing device may further include an on/off switch, a speaker for emitting an alert, and an eject button for ejecting the sensor out of the sensor slot.

In another aspect of the present application, a handheld device for testing saliva to measure at least one substance or physiological parameter of a human or animal subject may include: a housing; a sensor slot in the housing; a display on the housing; and a computer processor housed in the housing for generating initial data related to the substance or parameter from the saliva. The device may also include an eject button on the housing for ejecting a used sensor out of the sensor slot. The device may also include multiple buttons on the housing for controlling the handheld device. The device may also include a wireless transmitter for transmitting the initial data to an additional computer processor separate from the handheld device.

In another aspect of the present application, a saliva sensor for use with a saliva testing device to measure at least one substance or physiological parameter of a human or animal subject may include: a bottom layer; multiple electrodes applied to the bottom layer; a top layer; at least one microfluidic channel between the bottom layer and the top layer, for directing saliva from one end to an opposite end of the saliva sensor; and a chemically functionalized mesh embedded between the bottom layer and the top layer to facilitate movement of saliva along a length of the saliva sensor. The saliva sensor may also include an insulating layer including a hydrophobic, dielectric material. In some embodiments, the saliva sensor may include multiple microfluidic channels, and the saliva sensor may thus be configured for measuring at least two substances or physiological parameters of the subject.

In yet another aspect of the present invention, a tangible computer readable medium may store instructions for performing a method for testing saliva to measure at least one substance or physiological parameter of a human or animal subject. The method may include receiving initial saliva data from a saliva testing device, the initial saliva data related to the at least one physiological parameter of the subject, and processing the initial saliva data to provide final measurement data describing the at least one substance or physiological parameter.

These and other aspects and embodiments are described in greater detail below, in relation to the attached drawing figures.

BRIEF DESCRIPTION OF THE DRAWINGS

FIG. 1B is a diagrammatic representation of a saliva measurement system provided in the form of a kit, according to one embodiment;

DETAILED DESCRIPTION OF THE INVENTION

This application is generally directed to systems, devices and methods for testing saliva to measure levels of one or more substances and/or one or more physiological parameters in, or of, a human or animal subject. According to various embodiments, saliva may be used to test for any suitable substance or substances or any parameter or parameters. Although much of the following discussion focuses on testing for hydration of a human subject, the same or alternative embodiments may be used for any of a large number of other measurements. Just a few examples of such measurements include, but are not limited to, hydration, lactate level, ketones, glucose, glycerides, sodium, potassium, calcium, magnesium, chlorides, phosphates, caffeine, melatonin, c-reactive protein, chemokines, cytokines, troponin, cortisol, creatinine kinase, insulin, beta hydroxyl butyrate, iron, ferritin, salivary amylase and oxalic acid and the like. In some embodiments, the system and method may be used to measure multiple substances or parameters, such as any combination of the substances/parameters just listed. And although it will not be repeated continuously throughout, any embodiment described for use with a human subject may alternatively be used for an animal subject (e.g., veterinary medicine, research, etc.).

In general, the system described herein includes a saliva sensor, a handheld device, and a computer processor, which may take the form of a computer application on a medical device. Each of these three primary components may also be provided separately as a saliva testing device, and all three components will be described in detail below.

Figure 1A:
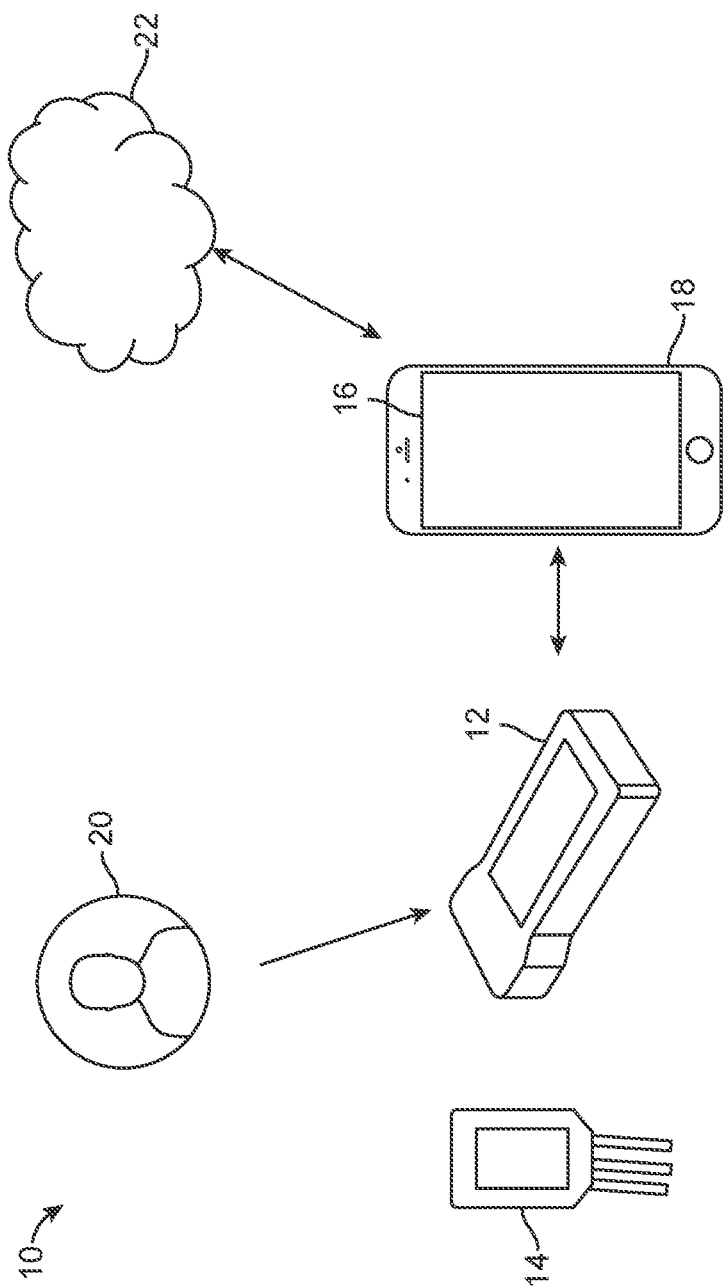
FIG. 1A is a perspective view of a saliva measurement system, according to one embodiment.

Referring now to FIG. 1A, in one embodiment, a saliva testing system 10 may include a handheld device 12, a sensor 14 (also referred to as a "strip" or "test strip") and a computer application 16, which may be located on a mobile computing device 18. In FIG. 1A, as in all figures provided in this application, features are not necessarily drawn to scale. For example, in this illustration, sensor 14 is disproportionately large, compared to handheld device 12 and mobile computing device 18. Furthermore, although computer application 16 will be referred to herein as an "application," this component of system 10 may include any computer software and/or hardware capable of receiving and processing data. In one form, computer application 16 is an application (or "app") that may be downloaded on any suitable mobile computing device 18, such as but not limited to a smart phone, tablet, or the like, or any other suitable computing devices, such as but not limited to a laptop computer, desktop computer, medical monitoring device or the like.

As will be described in greater detail below, one end of sensor 14 is configured to be inserted into a sensor slot on handheld device 12. A test subject 20 (or "user") then deposits saliva onto the opposite, free end of sensor 14, while sensor 14 is still inserted into handheld device 12. Sensor 14 moves the saliva across its surface via microfluidic channels and/or other mechanism(s) and measures at least one characteristic of the saliva. Handheld device 12 then reads data related to this measurement (or measurements) off of sensor 14. Handheld device 12 transmits data wirelessly or via a wired connection to application 16 via mobile device 18. Test subject 20, physicians, coaches, family members and/or any other suitable people may then access the data via mobile device 18. For example, in one embodiment test subject 20 may be given a hydration score, which she can read off of mobile device 18. In some embodiments, mobile device 18 may also send data to the cloud 22 for storage and/or further processing. Each of these functions will be described in further detail below.

With reference to FIG. 1B, a diagrammatic illustration of saliva testing system 10, in the form of a kit, is provided. This illustration shows handheld device 12, a box 15 of sensors 14, a USB cable 24 and a representation of computer application 16. In some embodiments, system 10 may be provided as such a kit or as a similar kit containing the same or similar components, along with instructions for use.

Handheld device 12 stimulates and acquires signals from sensor 14, performs signal processing, and transmits the data to computer application 16, for example via Bluetooth low energy or via USB cable 24. Handheld device 12 may include a display 26, which may provide information to test subject 20. For example, display 26 and/or a speaker (not shown) on handheld device 12 may alert test subject 20 when a sensor 14 is properly and completely inserted into handheld device 12, when a saliva measurement has started, when a saliva measurement has been completed, when a sufficient amount of saliva has been collected and tested, and/or the like. Handheld device 12 may also be configured to recognize different types of sensors 14, for example sensors configured to test for different parameters, such as a hydration sensor 14 versus a potassium sensor. Similarly, handheld device 12 may include a lock-out function that senses whether a sensor is new/unused versus used or approved for use with system 10 versus a counterfeit or defective sensor. The identification and lock-out function prevents handheld device 12 from activating if a sensor is inserted that is used, counterfeit, broken, etc. Handheld device 12 may also be configured to receive software updates wirelessly. Handheld device 12 may be powered by rechargeable or disposable batteries, according to different embodiments, and it may also include a battery level indicator, which may be displayed on display 26 or separately.

Figure 2A:
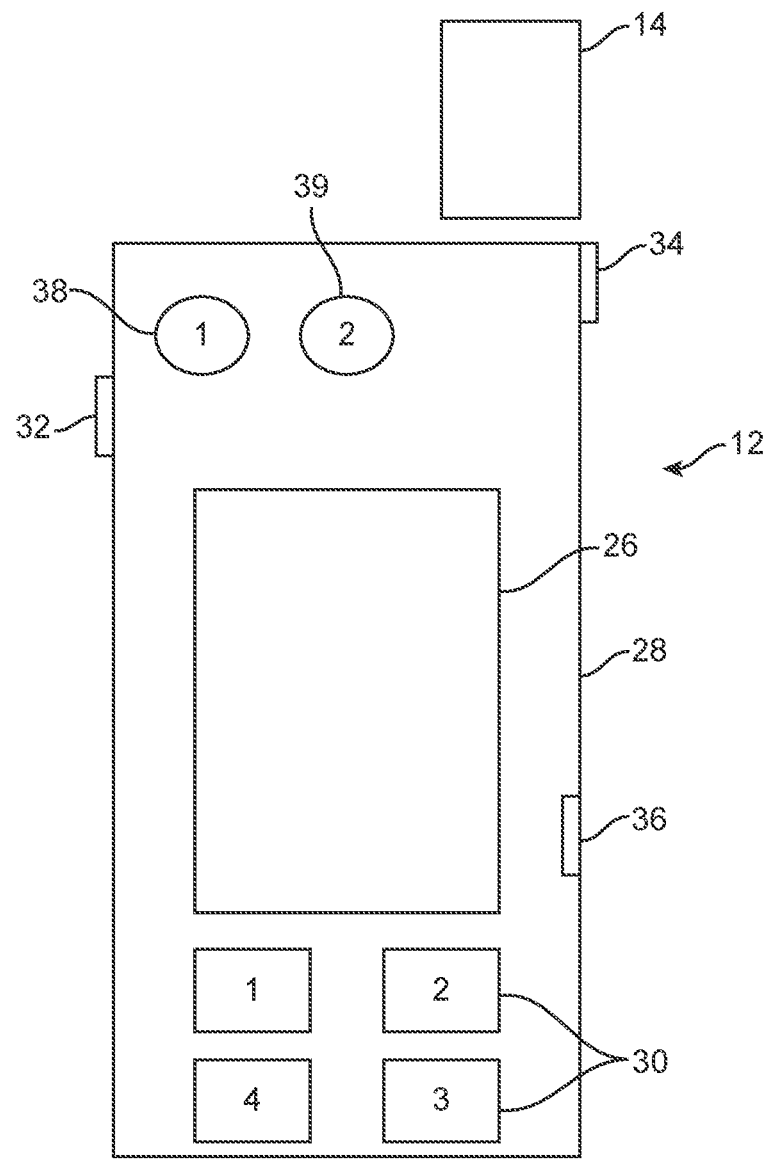
FIG. 2A is a diagrammatic representation of a handheld device and sensor of a saliva measurement system, according to one embodiment.

FIG. 2A is a diagrammatic representation of handheld device 12 and sensor 14. In this embodiment, handheld device 12 includes a housing 28, LCD display 26, multiple buttons 30 for controlling various functionality, a power switch 32, a sensor ejection button 34, a speaker 36, an LED battery level indicator 38 and an LED Bluetooth status indicator 39. In one embodiment, sensor 14 may be inserted into a slot (not visible) on the top of housing 28. When a sensing and measuring process is completed, sensor 14 can be ejected from housing 28 using sensor ejection button 34. In alternative embodiments, sensor 14 may be manually removed by the user after the test is complete. This is merely one embodiment of handheld device 12, and alternative embodiments may include fewer, different or additional features.

Figure 2B:
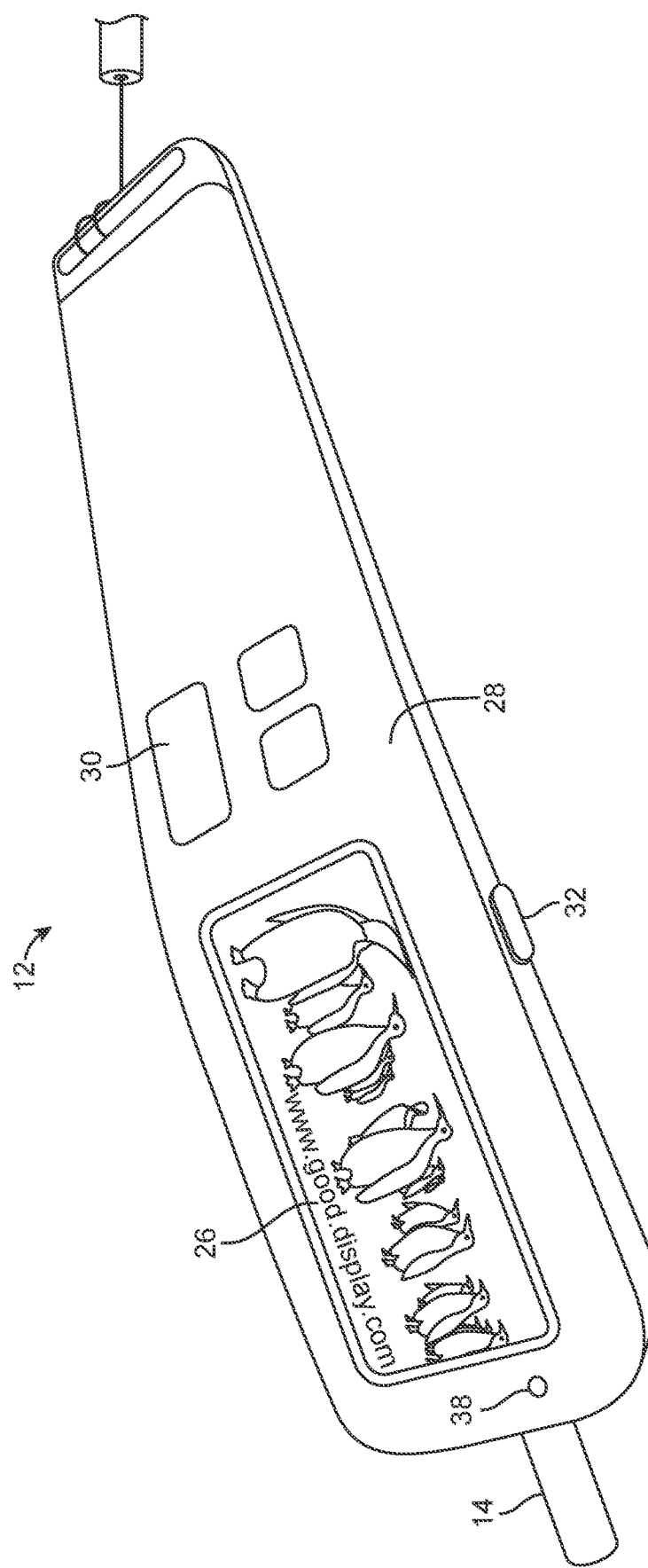
FIGS. 2B-2E are perspective, front, back and top/perspective views, respectively, of a handheld device and sensor of a saliva measurement system, according to one embodiment.
Figure 2C:
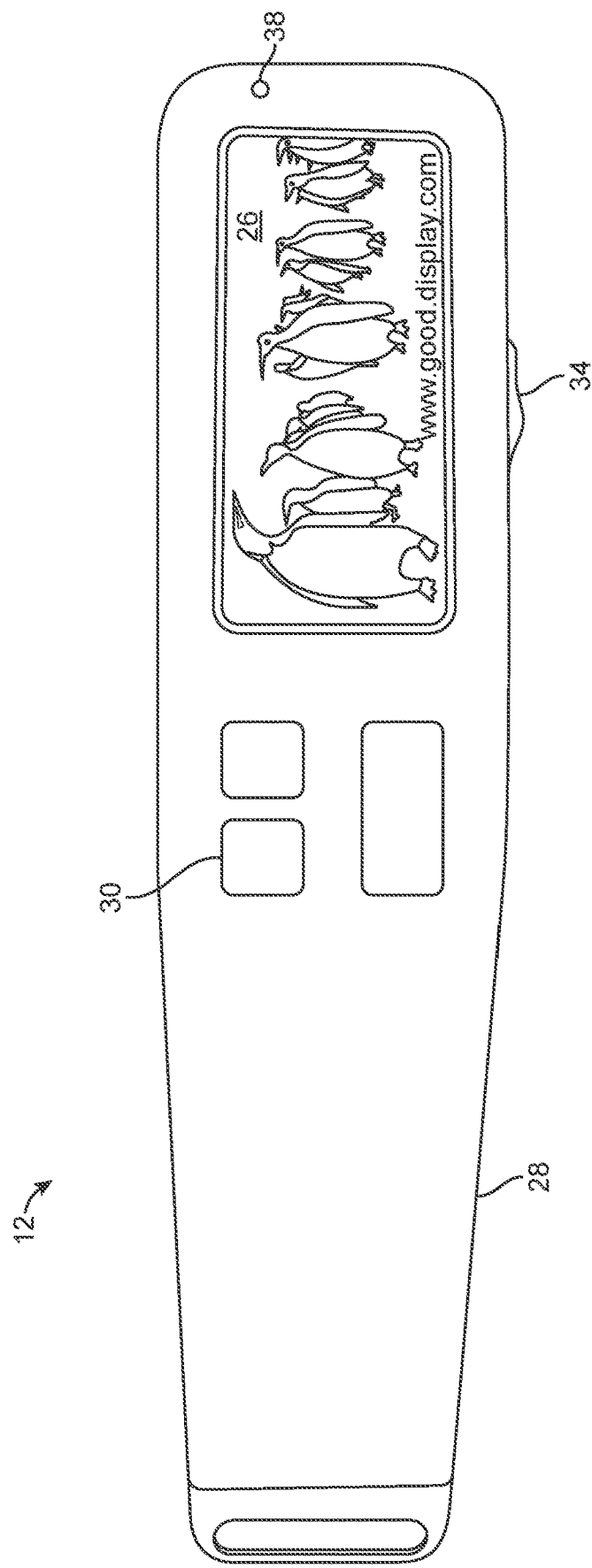
Figure 2D:
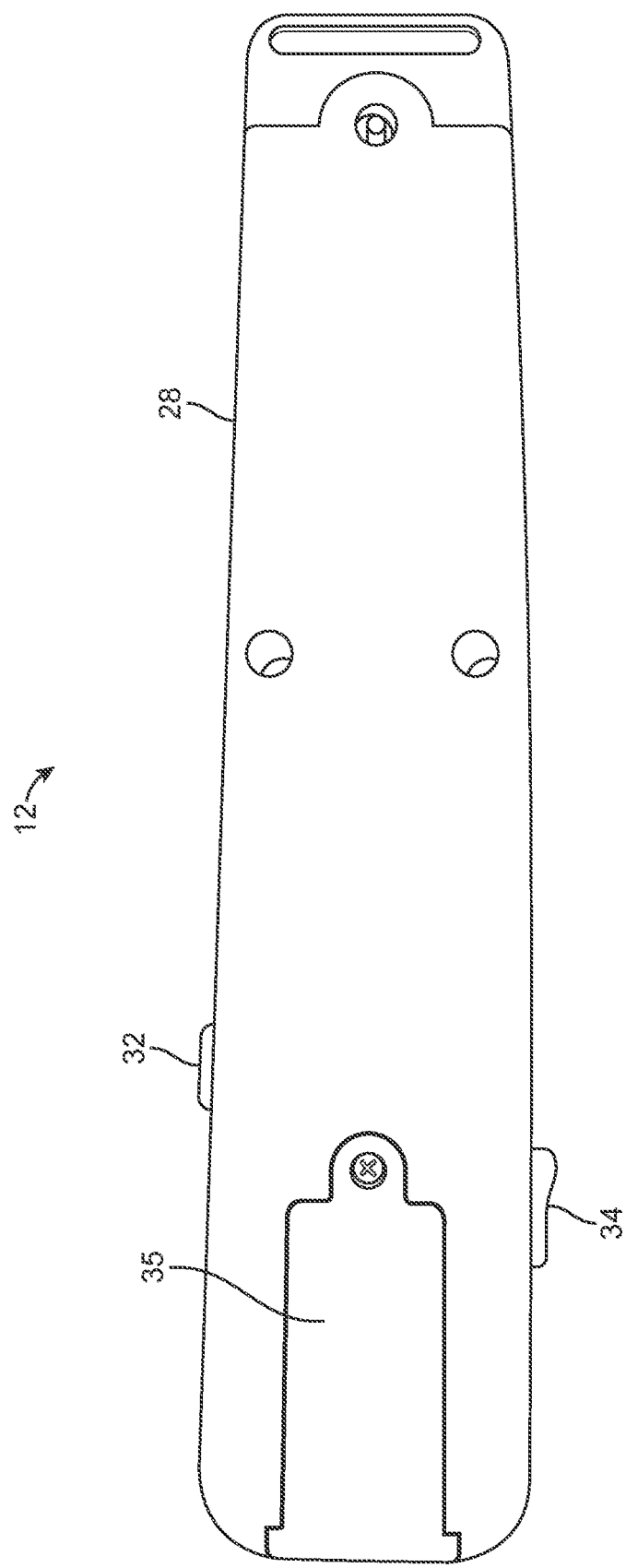
Figure 2E:
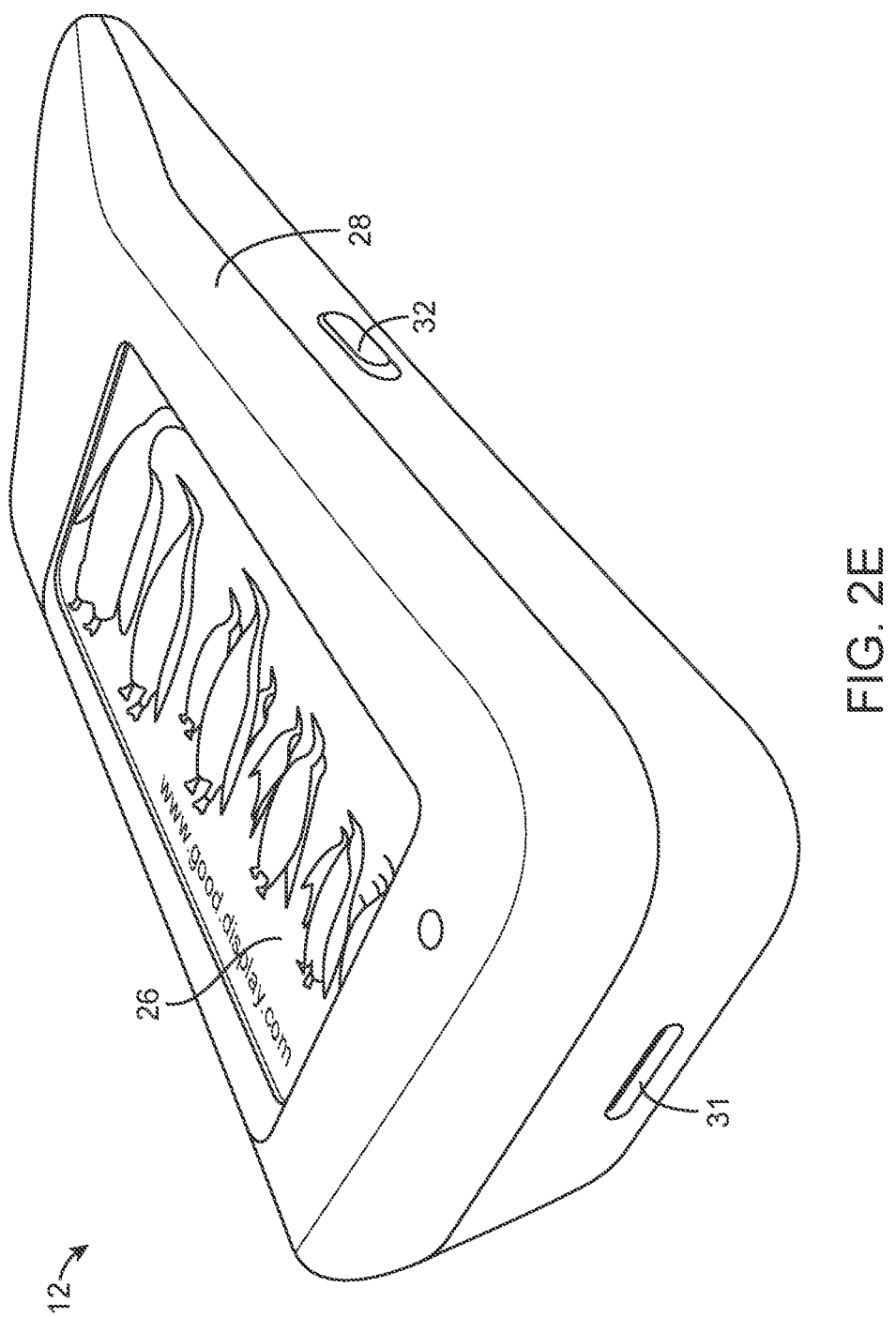

FIGS. 2B-2E are perspective, front, back and top/perspective views, respectively, of one embodiment of handheld device 12, shown with one embodiment of sensor 14 in FIG. 2B. This embodiment includes three buttons 30 on the front of housing 28, one of which is an up/down toggle switch. As shown in FIG. 2D, the back of housing 28 may include a battery cover 35, inside of which is a battery housing for holding one or more rechargeable or disposable batteries for powering handheld device 12. FIG. 2E shows a sensor slot 31 in housing 28, which was mentioned previously. In use, one end of sensor 14 is inserted into sensor slot 31, and saliva is collected on the opposite, "free" end of sensor 14 by contacting that free end with the subject's tongue, lips or any other part of the subject's mouth. This collection step may also be referred to as "depositing" saliva on sensor 14. In alternative embodiments, the saliva may be deposited indirectly, for example by collecting the saliva in a collection device and then depositing it on sensor 14. However, the direct collection method, where the free end of sensor 14 is contacted with the subject's tongue/mouth, may be advantageous for convenience, ease and speed of testing, reduction of contaminants in the saliva and/or other reasons.

Once the saliva is collected on the free end of sensor 14, it is transported at least partway across the length of sensor 14 via microfluidics on sensor 14. The saliva is then analyzed by handheld device 12, and sensor 14 is ejected from sensor slot 31 by pressing sensor ejection button 34 (FIGS. 2C and 2D). In an alternative embodiment, sensor 14 may simply be pulled out of sensor slot 31 manually after use, rather than ejected.

Figure 3:
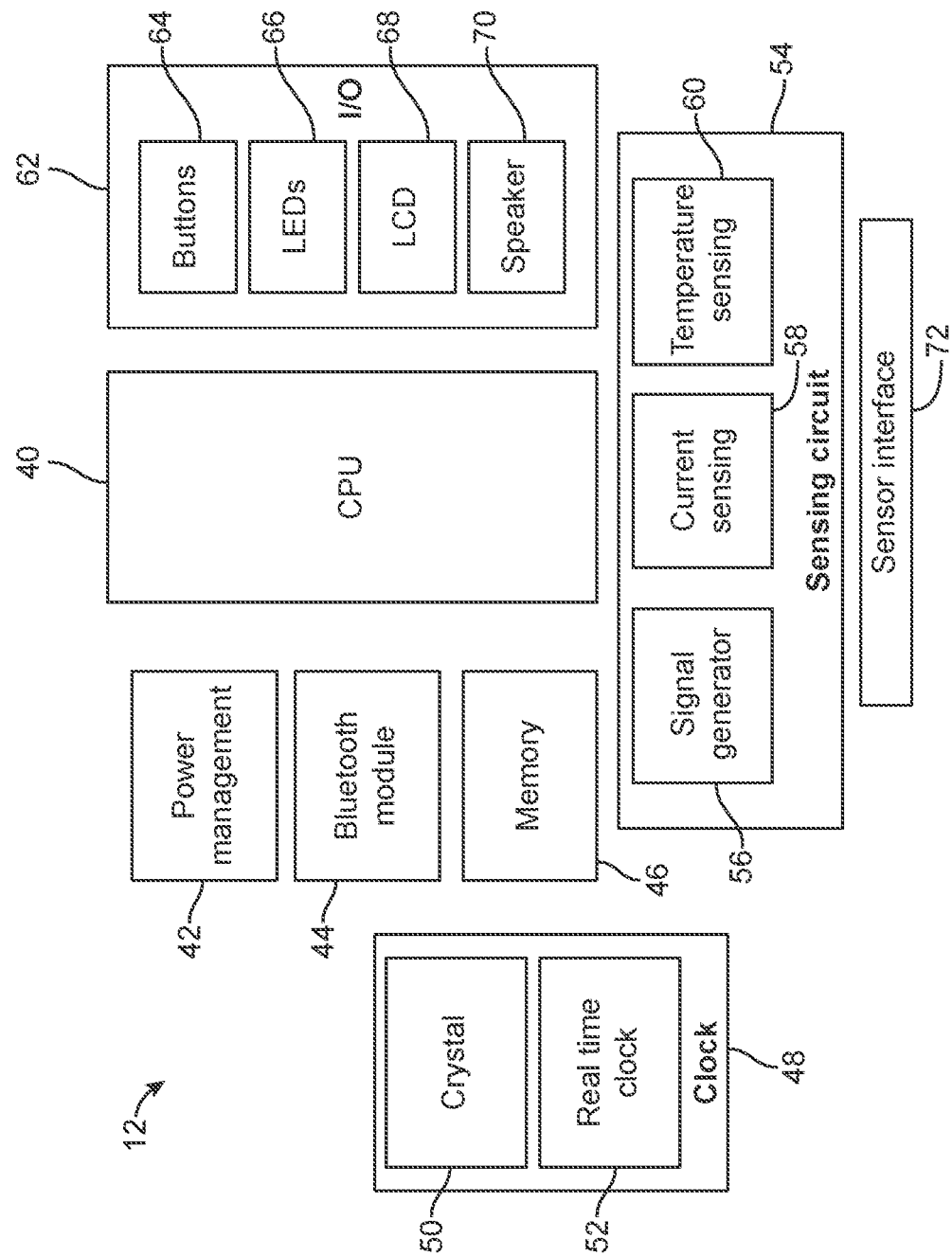
FIG. 3 is a block diagram of the internal components of a handheld device of a saliva measurement system, according to one embodiment.

FIG. 3 is a diagrammatic representation of the internal components of handheld device 12. In this embodiment, handheld device 12 includes: a central processing unit (CPU) 40; a power management module 42 for managing power and charging handheld device 12; a clock module 48 including a crystal 50 and a real time clock 52; a Bluetooth module 44 including a transceiver module and antennas; a memory 46 for storage of code and the user's measurement data; an input/output (I/O) management module 62 to control buttons 64, LEDs 66, LCDs 68 and a speaker 70 for interaction of the user with the device; a sensing circuit 54 that includes a signal generator 56, current sensing 58 and temperature sensing 60, and a sensor interface 72 that connects handheld device 12 and sensor 14.

In one embodiment, handheld device 12 is powered from single cell 1000 mAh Li-on battery. A buck switching regulator may be included, to convert battery voltage to 3.3V, with a maximum current of 1 A. A single on/off push button switch may be included, to turn on the system. The battery can be recharged on fast mode with up to 2 A current. A lightning connector may be used in some embodiments. An integrated Bluetooth module 44 may be included, which may be fully compatible with Bluetooth 5. Handheld device 12 may further include integrated 1M flash ROM and 512 kB RAM. The CPU may operate at 32 MHz. Some embodiments may include an external micro SD card storage for measurement storage. Clock module 48 may include a 32 MHz crystal 50. Real time clock 52 may be available for time stamp labelling of sensor measurement. LCD display 26 may be a touch screen LCD. Buttons 30 may be push buttons and may control any suitable functions of handheld device 12. Micro speaker 36 may be used to provide audible cues to indicate the start of a measurement, completion of a measurement an error during measurement and/or the like.

Figure 4:
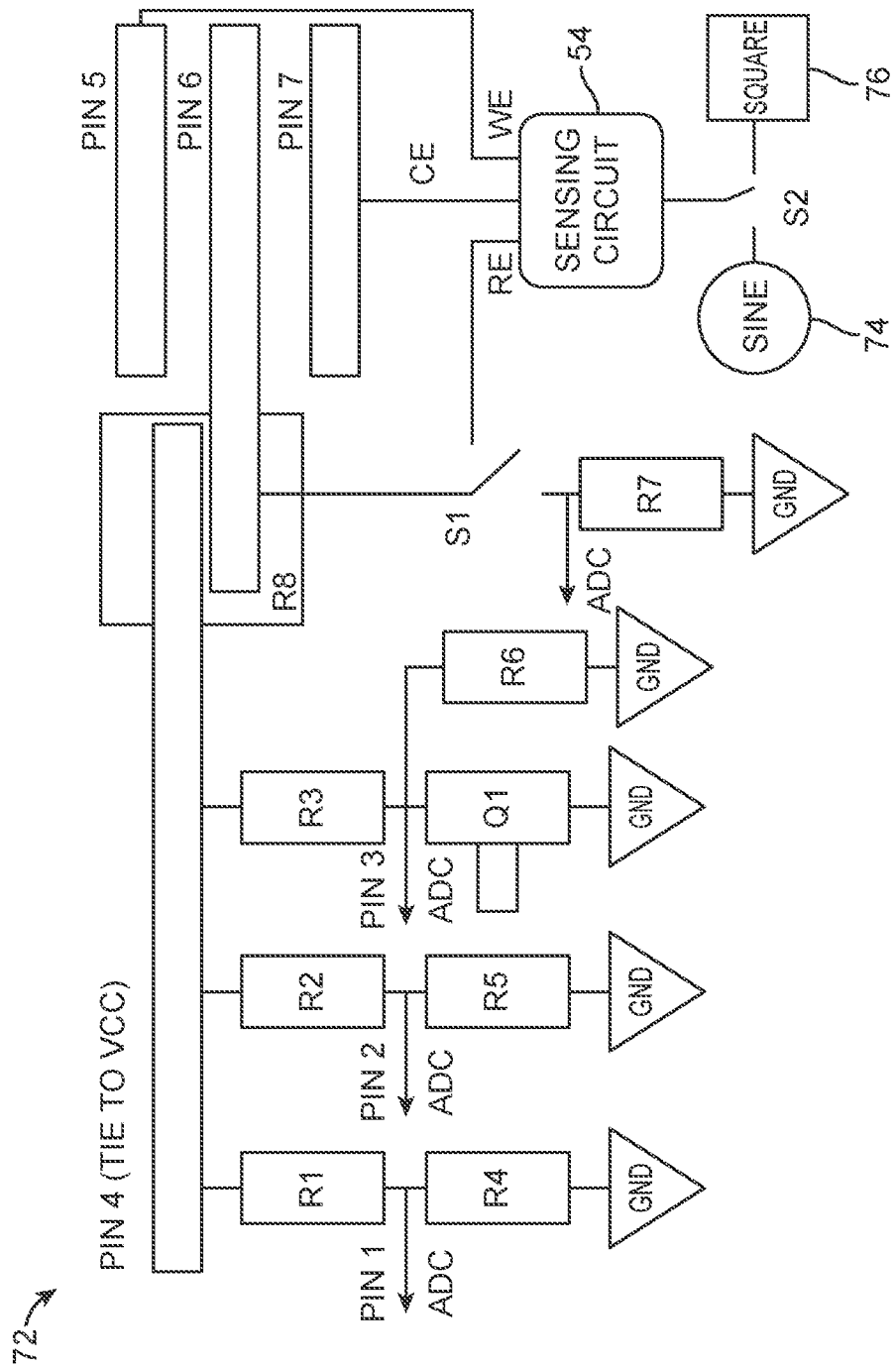
FIG. 4 is a diagram of a portion of the electronics of a handheld device of a saliva measurement system, according to one embodiment.

Referring to FIG. 4, sensor interface 72 may include a strip with seven connectors. In FIG. 4, R4, R5, R6, R7 are reference resistors. Q1 is an N type MOSFET, with maximum current greater than 1 A. S1 and S2 are analog switches, with maximum current above 100 mA. Sensing circuit 54 includes a sinusoidal signal generator 74 for hydration detection, with frequency up to 20 kHz and adjustable amplitude up to 200 mV. Sensing circuit may also include a square wave generator 76 for lactate and testosterone detection, with arbitrary on/off duty cycle and magnitude that varies from 50 mV to 700 mV. Sensing circuit 54 may be a three-electrode electrochemical circuit, which can be used for hydration and/or lactate/testosterone detection. The type of detection can be multiplex using analogue switching. Sensing circuit may also include on-board temperature sensor 60, as a reference for both electronic circuit performance and sensor strip temperature detection.

Figure 5A:
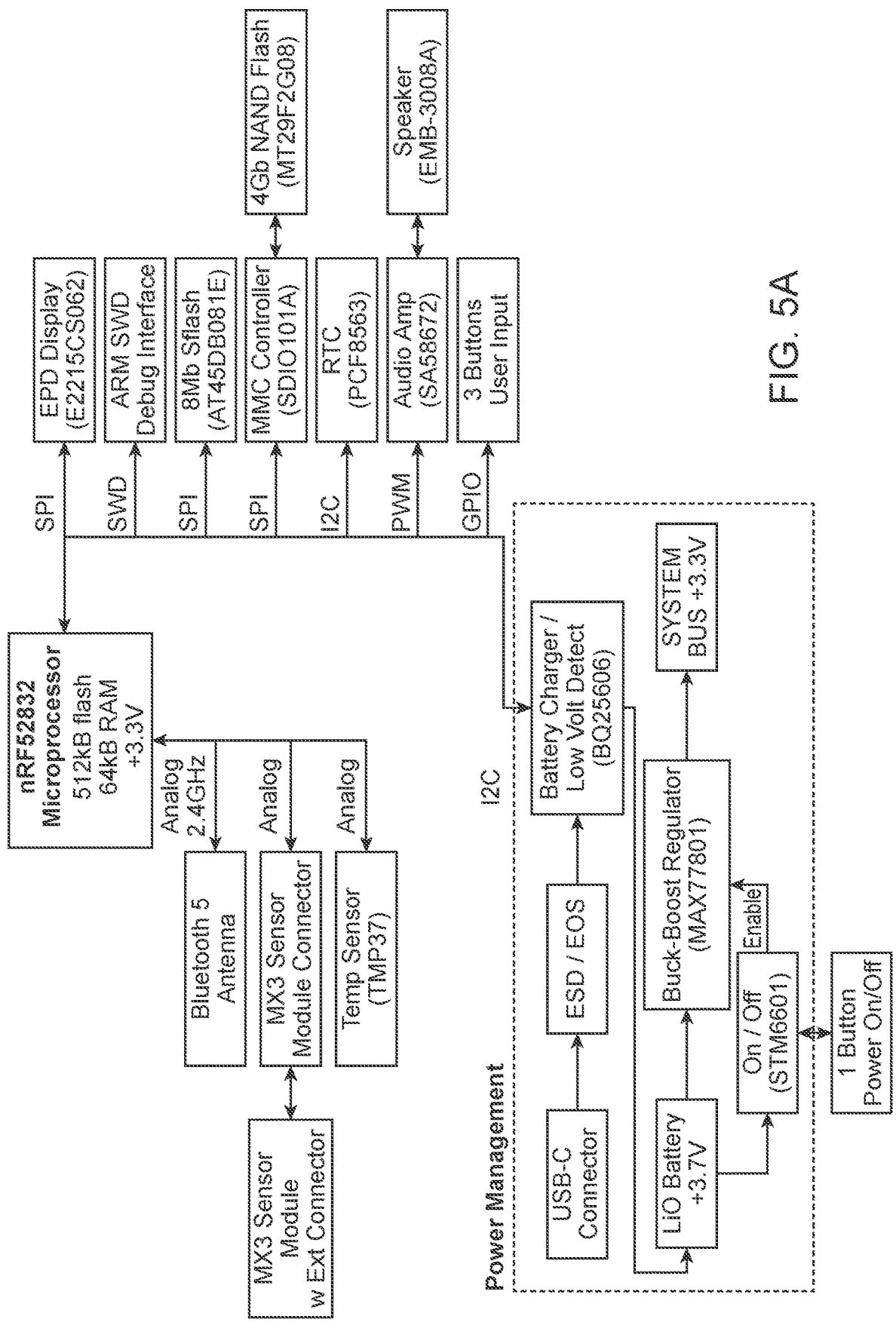
FIGS. 5A-5C are additional diagrams of portions of the electronics of a handheld device of a saliva measurement system, according to one embodiment.
Figure 5B:
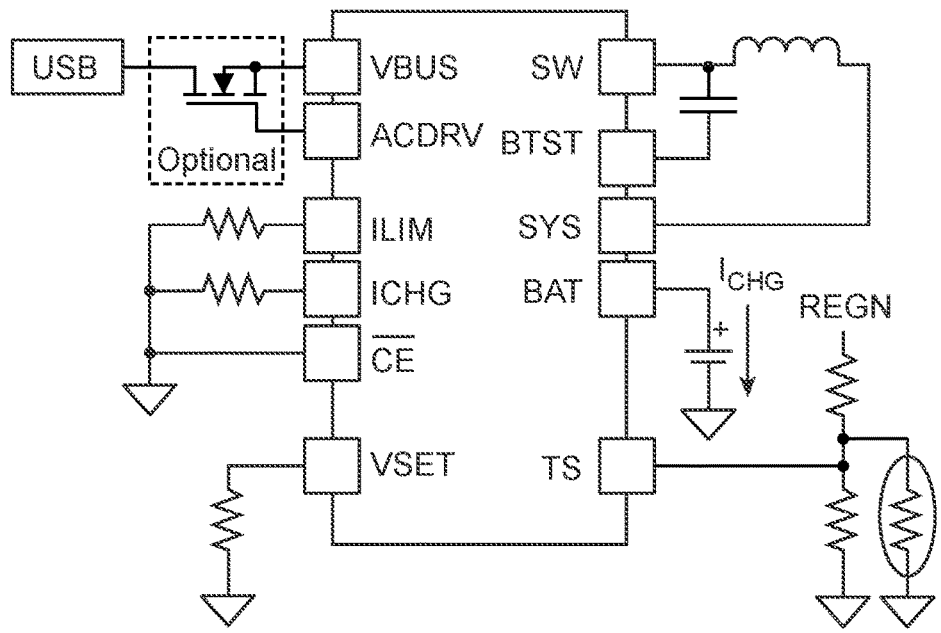
Figure 5C:
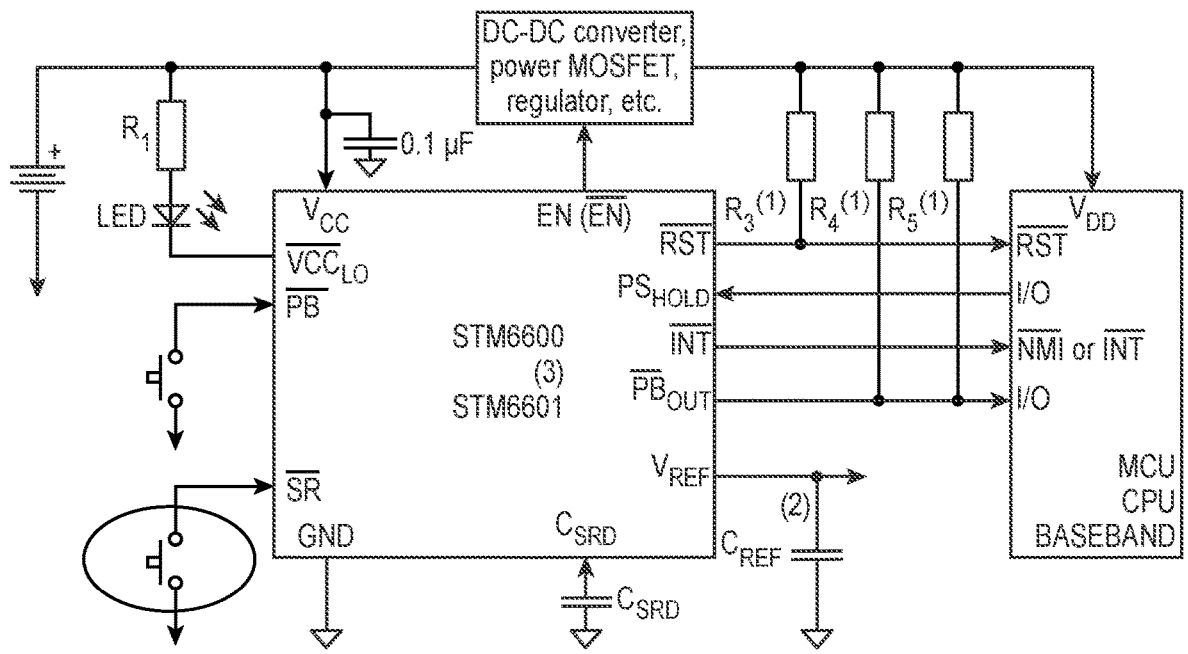

FIG. 5A is a more detailed hardware system diagram for handheld device 12, according to one embodiment. FIG. 5B is circuit diagram for a battery charger circuit for handheld device 12, according to one embodiment. FIG. 5C is a circuit diagram for a power on/off smart controller for handheld device 12, according to one embodiment.

Figure 6A:
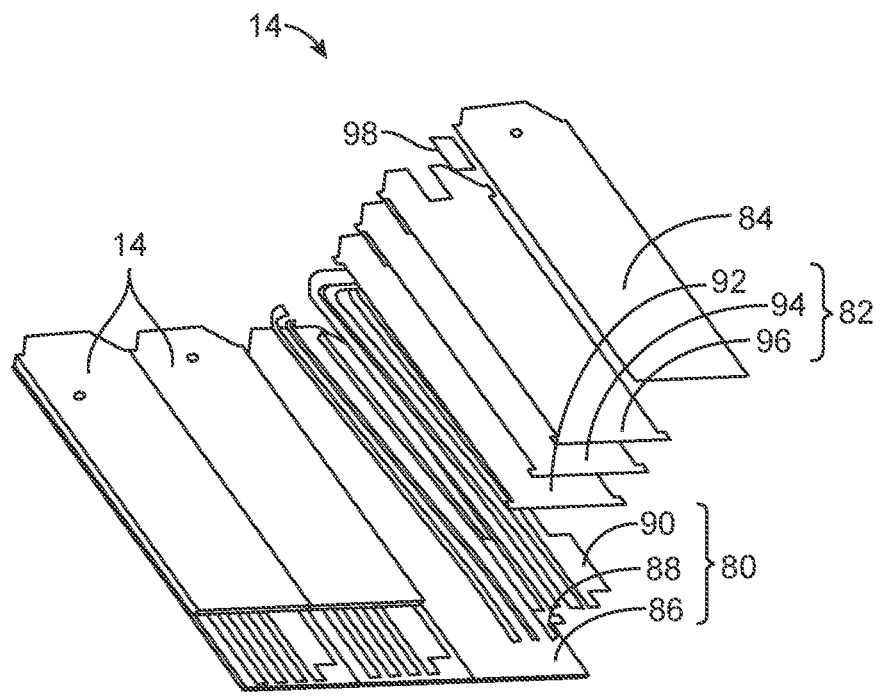
FIGS. 6A and 6B are perspective/exploded and assembled/side/top views, respectively, of a sensor of a saliva measurement system, according to one embodiment.
Figure 6B:
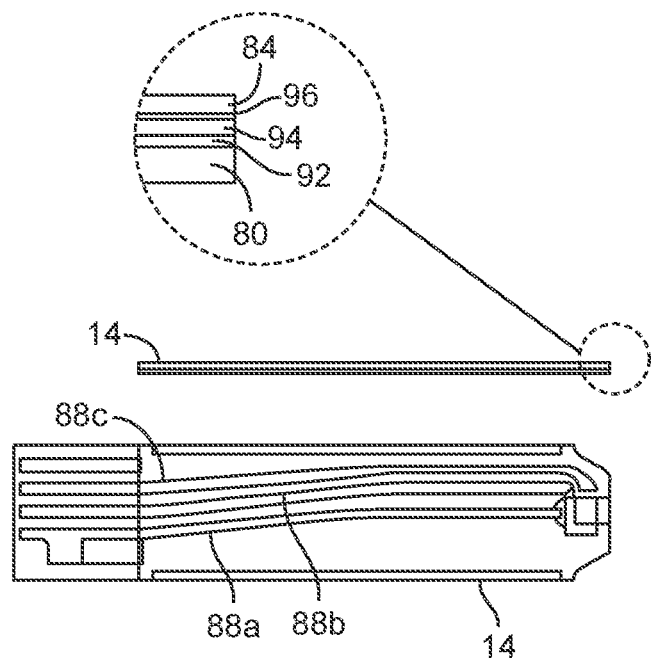

Referring now to FIGS. 6A and 6B, sensor 14 is shown in more detail. In general, sensor 14 is the sensing component of system 10. It measures the osmolality and/or osmolarity of a user's saliva and includes a saliva collector, a fluidic channel to deliver saliva to a sensing area, and multiple electrodes. FIG. 6A, shows three sensors 14—the two on the left are assembled, and the one on the right is shown in exploded view. The exploded view illustrates that sensor 14 may include three layers—a bottom layer is the electrode layer 80 (T1 in the figure), a middle layer is the spacer layer 82 (T2 in the figure), and a top layer is the cover 84 (T3 in the figure). In this embodiment, electrode layer 80 includes a bottom layer of polyethylene terephthalate (PET) 86, a middle layer of silver 88 and a top layer of carbon 90. The bottom layer 86 can be constructed of a variety of materials, such as carbon, polystyrene, polycarbonate, polyvinyl chloride resin, and polyester. In the illustrated embodiment, the bottom layer 86 is constructed of PET. The same variations of materials may be used in any of the other layers described below as being made of PET. Spacer layer 82 includes a bottom layer of pressure sensitive adhesive 92, a middle layer of PET 94 and a top layer of pressure sensitive adhesive 96. Cover 84 is made simply of one layer of PET in this embodiment. Sensor 14 also includes an enzyme mesh insert 98, for facilitating fluid flow along sensor 14. In alternative embodiments, sensor may include multiple fluidic channels and multiple sets of electrodes, to measure multiple molecules of interest.

In the illustrated embodiment, sensor 14 includes three electrodes, all of which are made of silver—in other words, the middle silver layer 88 of the electrode layer 80. Thus, for purposes of the description of FIGS. 6A and 6B, "silver layer" and "silver electrodes" will both use the reference label 88. In this embodiment, sensor 14 has three silver electrodes 88, two of which are for electrochemical measurement and one of which is for fluid detection. Silver electrodes 88, in general, are used to electronically determine the presence and/or amount of a substance (or "analyte") of interest present in a fluid sample. For example, electrodes 88 may be used to detect osmolarity of a saliva sample, which information may be used to determine hydration of a human or animal subject. Carbon layer 90 helps increase conductivity of silver electrodes 88.

In one embodiment, electrodes 88 are printed on bottom layer 86. In various alternative embodiments, Ag/AgCl, carbon inks (graphite), palladium, gold, platinum, iridium, doped indium tin oxide, stainless steel, and other suitable conducting materials may be used. Electrodes 88 may also be made of combinations of these materials. For example, one portion of an electrode 88 may be one material, and another portion of the same electrode 88 may be another material. Electrodes 88 may be arranged on bottom layer 86 in any desirable format.

FIG. 6B includes a top view of sensor 14 (bottom portion of figure), with layers removed to show detail of silver electrodes 88, a side view of sensor 14 (middle portion of figure), and a detailed side view of one end of sensor 14 (top magnified view). Dimensions for one embodiment are also labeled in this figure. As illustrated in the top view, sensor 14 may include a volume detection electrode 88a, a counter/reference electrode 88b and a working electrode 88c. Other embodiments and configurations are contemplated within the scope of the present disclosure.

Figure 7A:
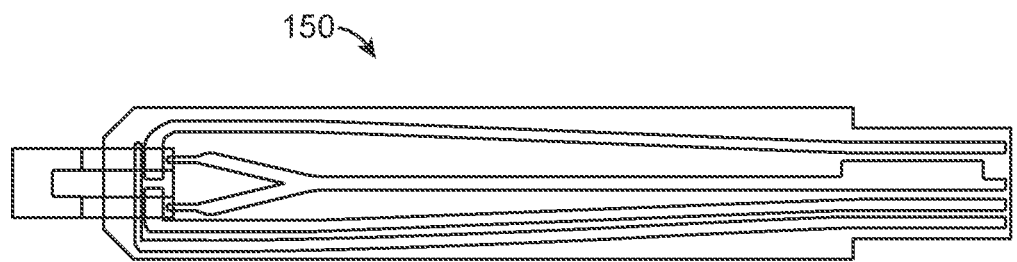
FIGS. 7A-7C are top views of various embodiments of sensor of a saliva measurement system.
Figure 7B:
Figure 7C:
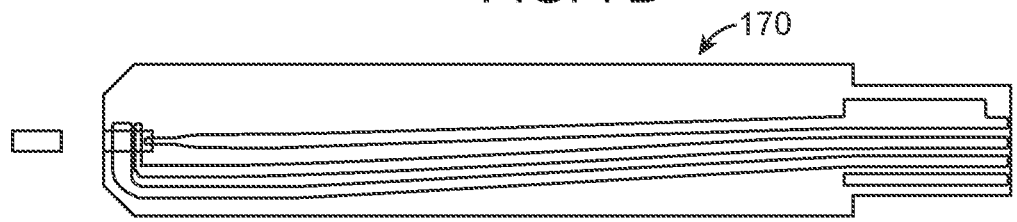
Figure 7D:
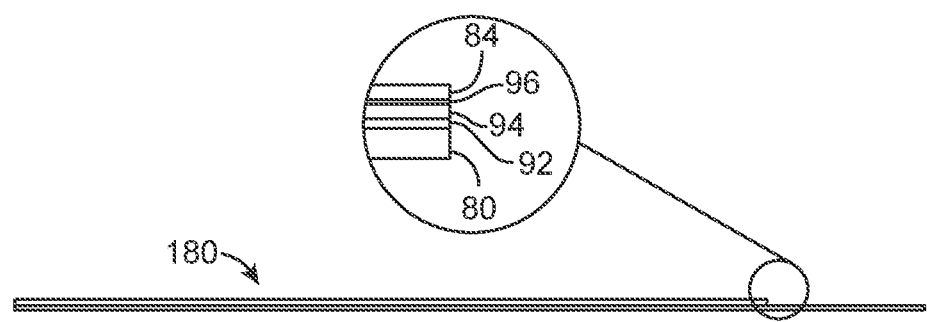
FIG. 7D are side and top views of a portion of a sensor of a saliva measurement system, according to one embodiment.
Figure 7D:
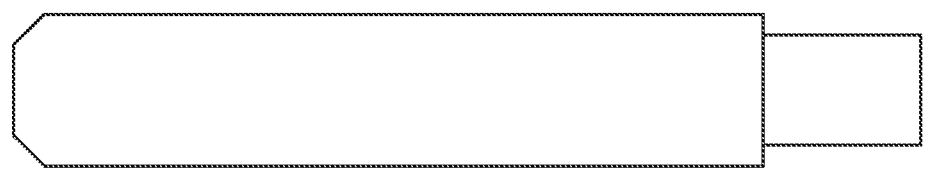

Referring now to FIGS. 7A-7D, various alternative embodiments of a sensor are shown. FIG. 7A is a top view of a sensor 150 having multiple microfluidic channels and a split mesh. FIG. 7B is a top view of a sensor 160 having separated channels. FIG. 7C is a top view of sensor 170 having one channel. And FIG. 7D shows a side view (top panel) and top view (bottom panel) of a substrate 180 of a sensor, according to one embodiment.

Figure 8:
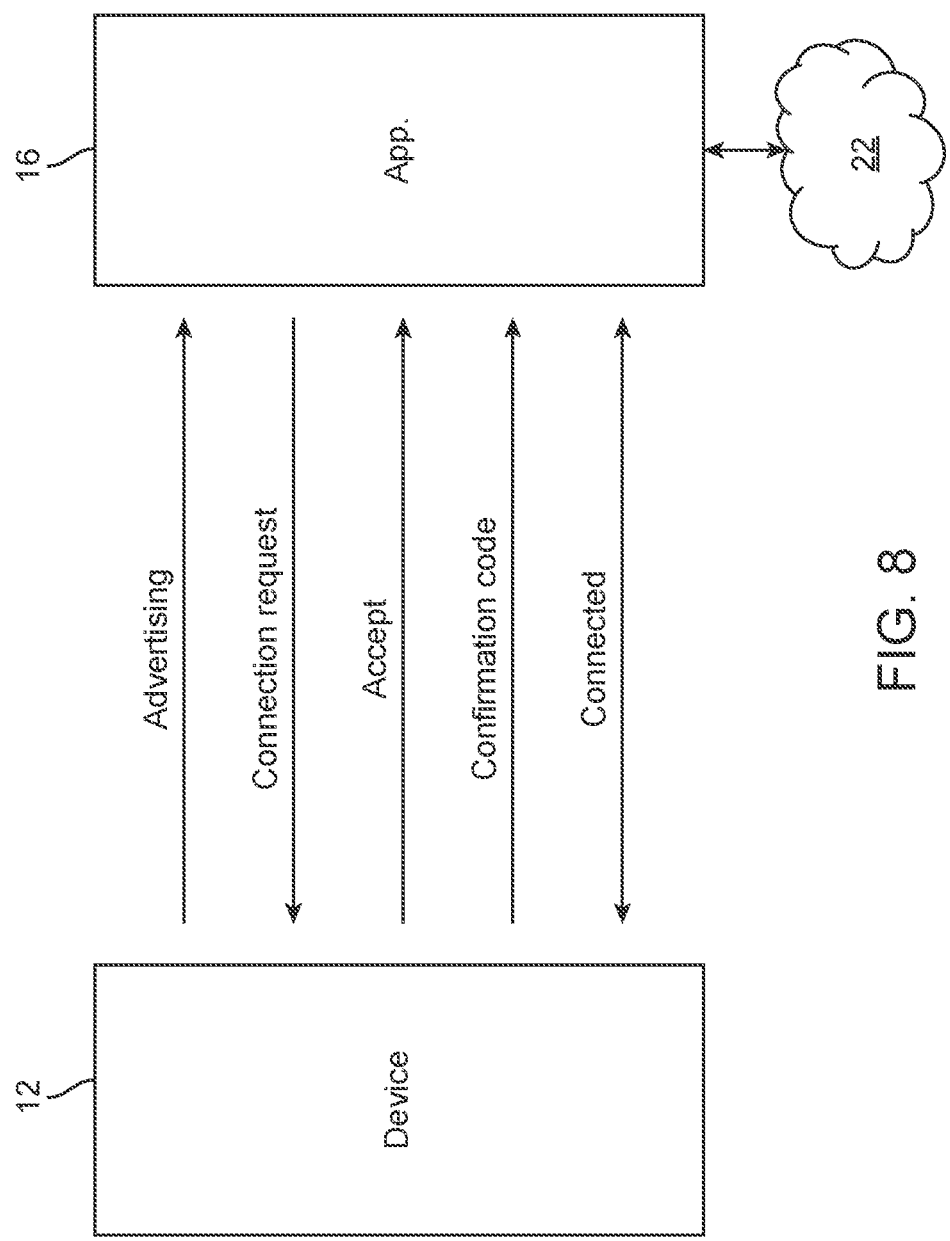
FIG. 8 is a flow diagram illustrating movement of information between a handheld device and a computer application of a saliva measurement system, as well as the cloud, according to one embodiment.

Referring now to FIG. 8, computer application 16, which may be located on mobile computing device 18, communicates with handheld device 12 and the cloud 22. Data pertaining to test subject 20 (e.g., personal information and measurement results) may be stored in the cloud 22. Any of a number of different types of information may travel back and forth between handheld device 12 and computer application 16. For example, initial data regarding tested saliva may be sent from handheld device 12 to computer application 16 for further processing. Advertising and/or any other suitable data may also be sent from handheld device 12 to computer application 16. Computer application 16 may send a connection request to handheld device 12, and an accept message may be transmitted back to computer application 16, along with a confirmation code. Handheld device 12 and computer application 16 may work together to establish the connection between the two.

Figure 9A:
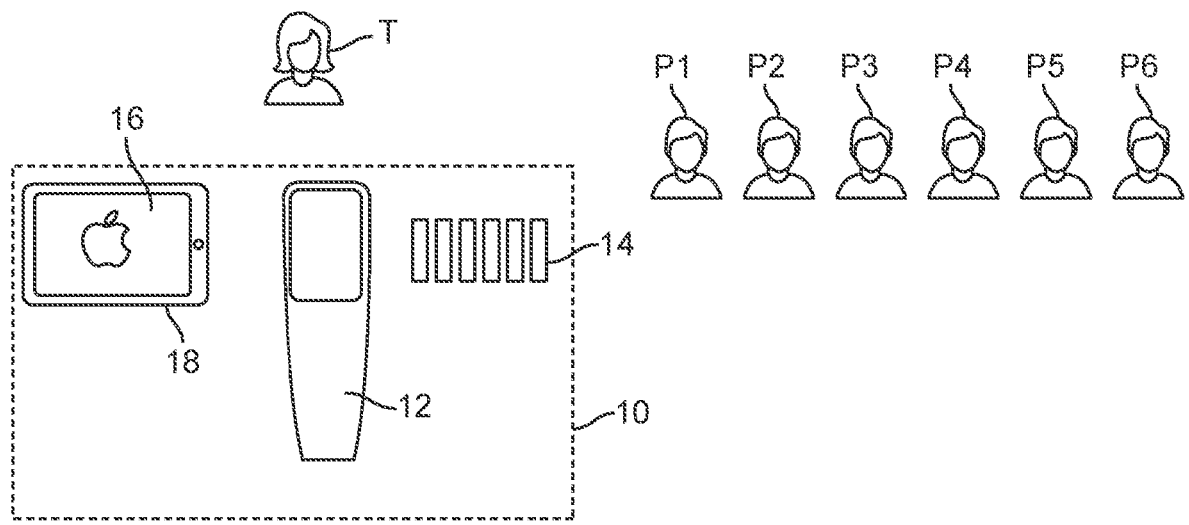
FIGS. 9A-9I are diagrammatic representations illustrating a method of using a saliva measurement system, according to one embodiment.

With reference now to FIGS. 9A-9I, a method for using saliva testing system 10, according to one embodiment, will now be described. Referring to FIG. 9A, in this embodiment, a trainer T tests saliva from six players P1-P6, although only Player 1's test will be described. In this embodiment, the trainer T uses an iPad mobile tablet computing device 18, with computer application 16 loaded onto it, along with handheld device 12 and multiple sensors 14. As mentioned above, system 10 may be provided in a kit form in some embodiments, and sensors 14 may be provided in a box, packet or other container.

Figure 9B:
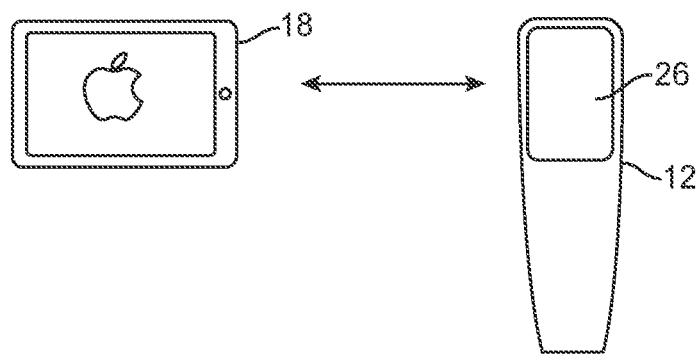
Figure 9C:
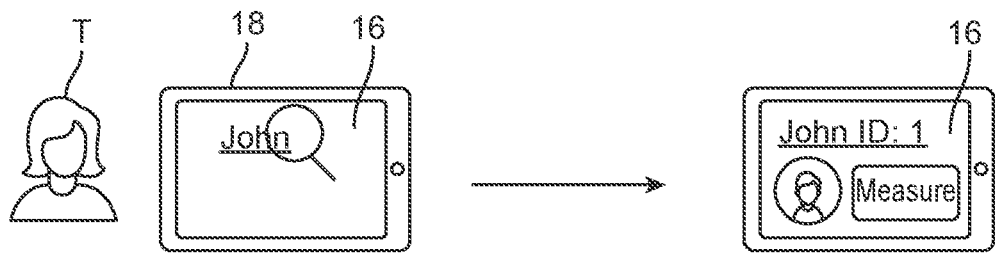
Figure 9D:
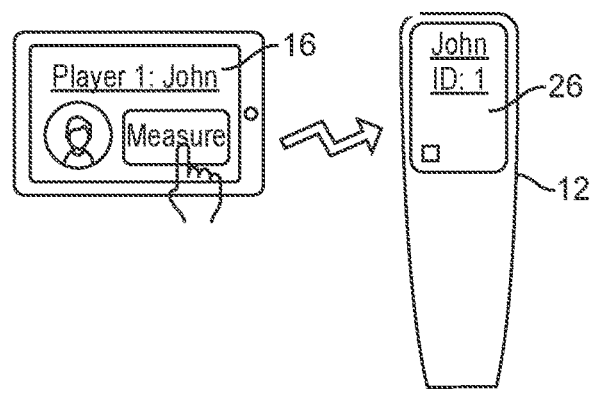

As illustrated in FIG. 9B, the trainer T turns on handheld device 12, opens and logs onto computer application 16, and handheld device 12 and application 16 pair with one another. This may be done automatically, for example if an auto-connect function is enabled, or may be done manually by the trainer T. Each handheld device 12 may include a unique identifier, such as a Bluetooth low energy identifier, which may facilitate pairing and ensure security. The trainer T may also scan a QR code on the box of sensors, for example for security and quality control reasons. Referring to FIG. 9C, the trainer T may next type a name and/or other identifier of Player1 P1 on the computer application 16 on the mobile computing device 18. Computer application 16 may display an image of Player1 P1 with a MEASURE button. As shown in FIG. 9D, the trainer T may then activate the MEASURE button, at which point computer application 16 may transmit a signal to handheld device 12, telling the latter that Player1 P1 is being measured. Handheld device 12 may display the name and ID of Player1 P1 on the LCD display 26.

Figure 9E:
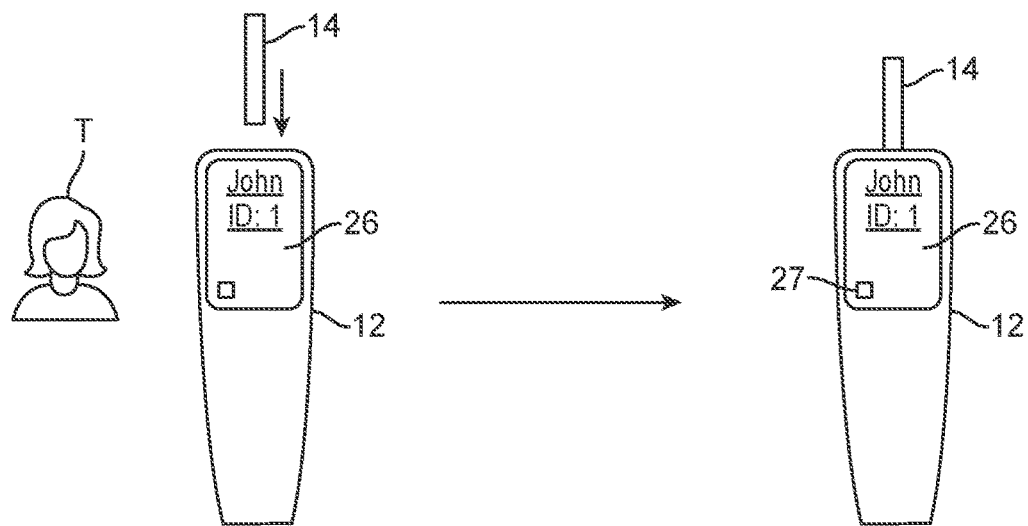

As shown in FIG. 9E, the trainer T then inserts a sensor 14 into handheld device 12, which detects that sensor 14 has been inserted. Display 26 may include an indicator 27 that shows when sensor 14 is ready for a measurement. Indicator 27 may change colors or simply appear on display 26 when sensor 14 is fully and properly inserted. If there is no player information when sensor 14 is inserted, handheld device 12 may alert the trainer T to look for the player information on computer application 16 before proceeding. The alert may be via visual and/or audio display.

Figure 9F:
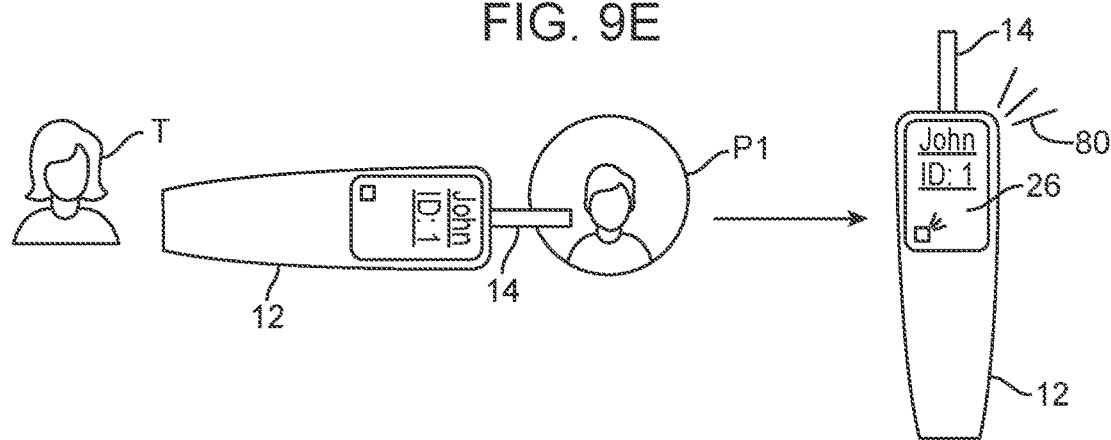
Figure 9G:
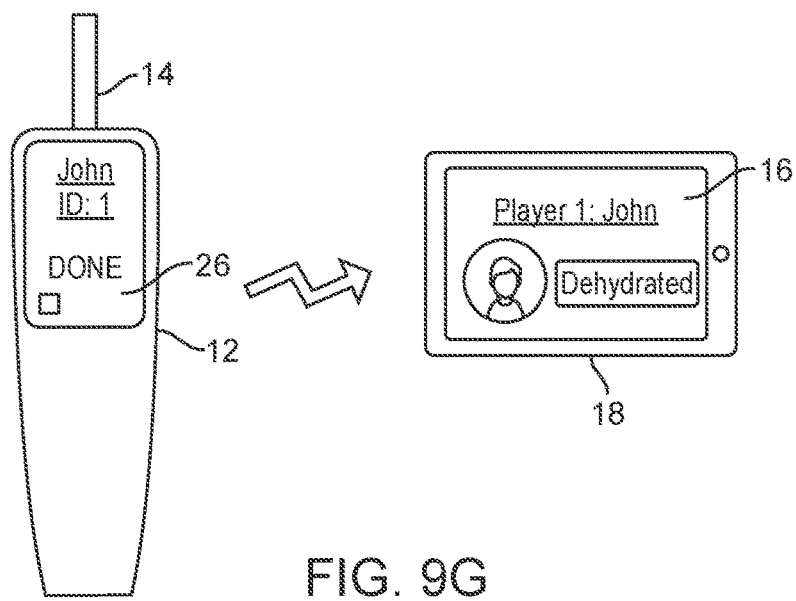
Figure 9H:
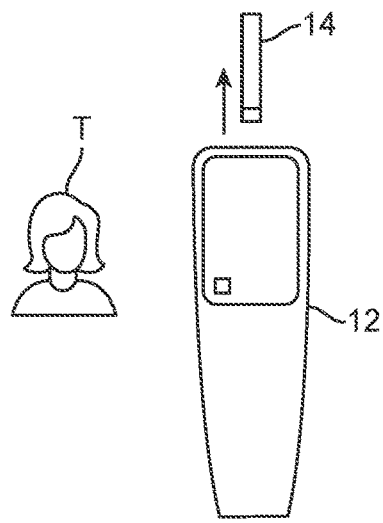
Figure 9I:
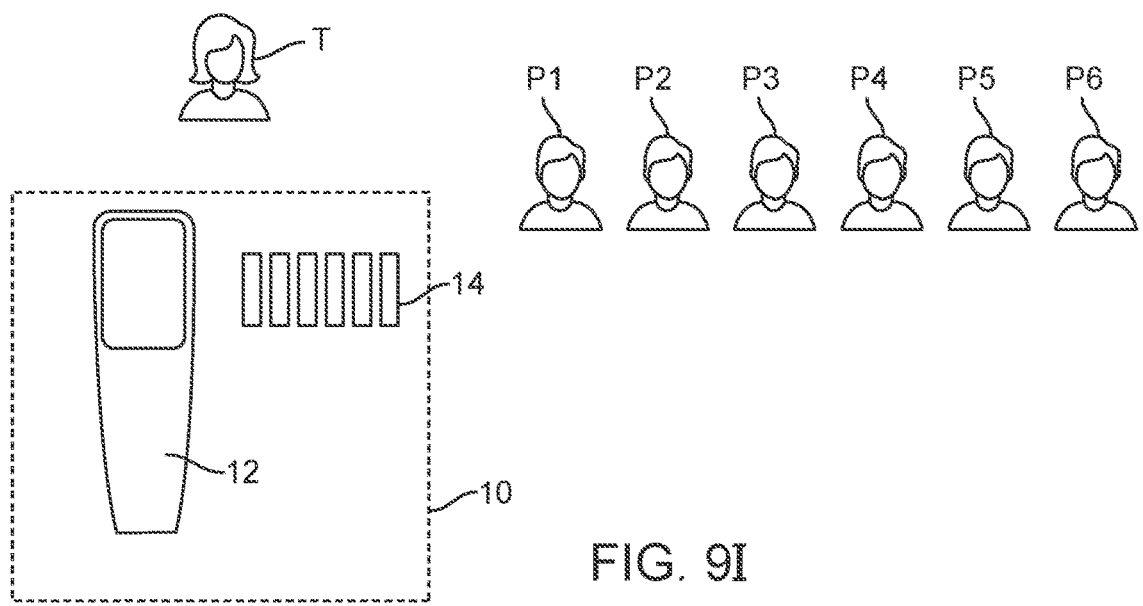

Referring next to FIG. 9F, the trainer T then places the free end of sensor 14 in Player1's mouth to collect a saliva sample. Handheld device 12 detects if there is a sufficient amount of saliva in sensor 14. If there is enough saliva, handheld device 12 performs the reading automatically (for example in 1-3 seconds). Handheld device 12 may play a beep sound 80 to let the trainer T know the measurement has started. Referring to FIG. 9G, upon hearing beep 80, the trainer T may remove sensor 14 from Player1's mouth and wait for approximately five seconds. After five seconds (or other appropriate period of time in alternative embodiments), handheld device 12 may display DONE and/or play a sound to indicate the measurement has finished. Handheld device 12 may at this point transmit initial data to computer application 16 on mobile computing device. Computer application 16 then processes the initial data and displays hydration status of Player1 P1. Finally, as illustrated in FIG. 9H, the trainer T ejects sensor 14 from handheld device 12. It is important that sensor 14 not be reused by Player 1 P1 or any other player. Referring to FIG. 8I, the steps outlined above may then be repeated by the trainer T for as many other players P2-P6 as desired.

Figure 10A:
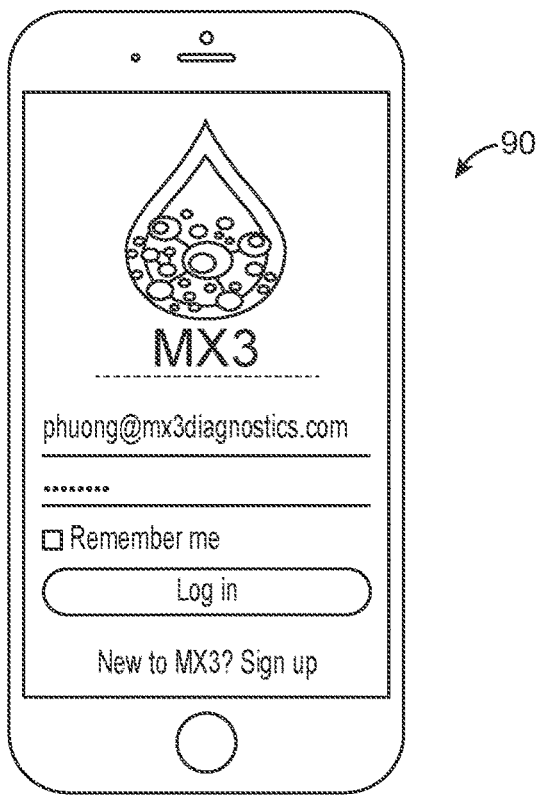
FIGS. 10A-10L are screen shots illustrating a method of using a computer application of a saliva measurement system, according to one embodiment.

Referring now to FIGS. 10A-10N, a series of screen shots of graphical user interfaces (GUIs) are shown, illustrating displays provided by computer application 16 to a user, according to one embodiment. These screen shots illustrate one method for progressing through computer application 16 during a saliva/hydration measurement of a player. This is only one exemplary method and series of interfaces, however, and should not be interpreted as limiting the scope of the present disclosure.

Figure 10B:
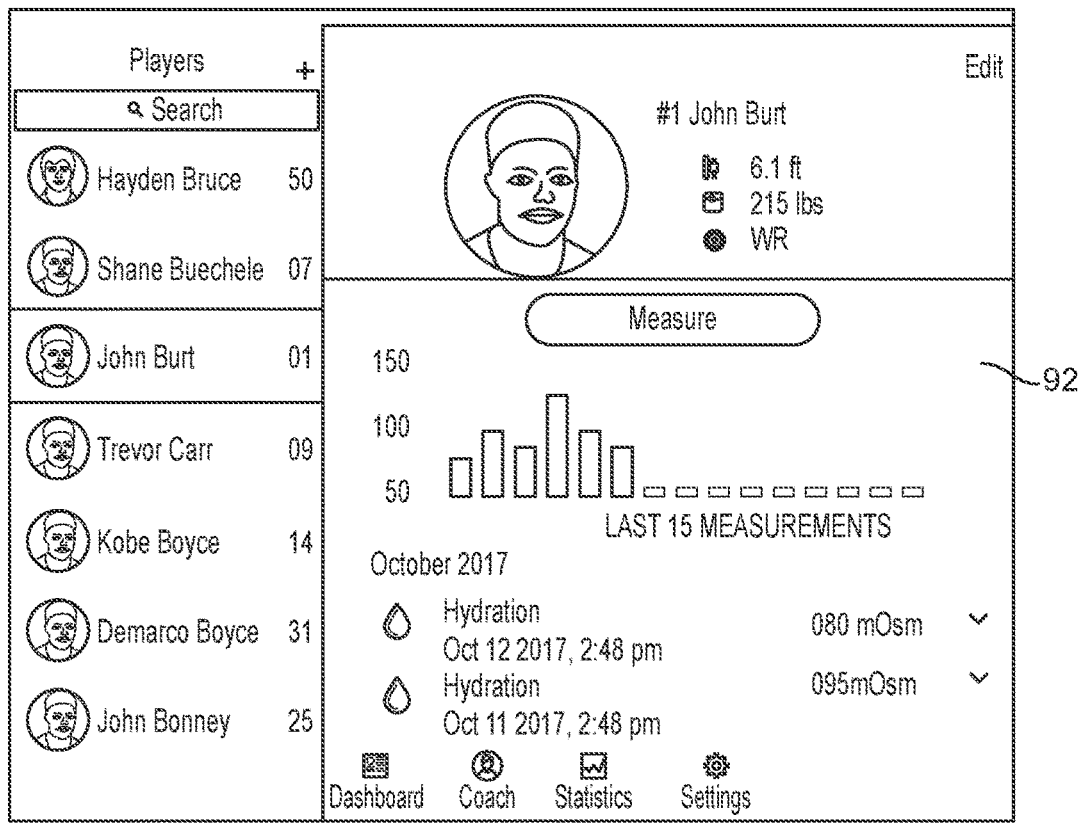
Figure 10C:
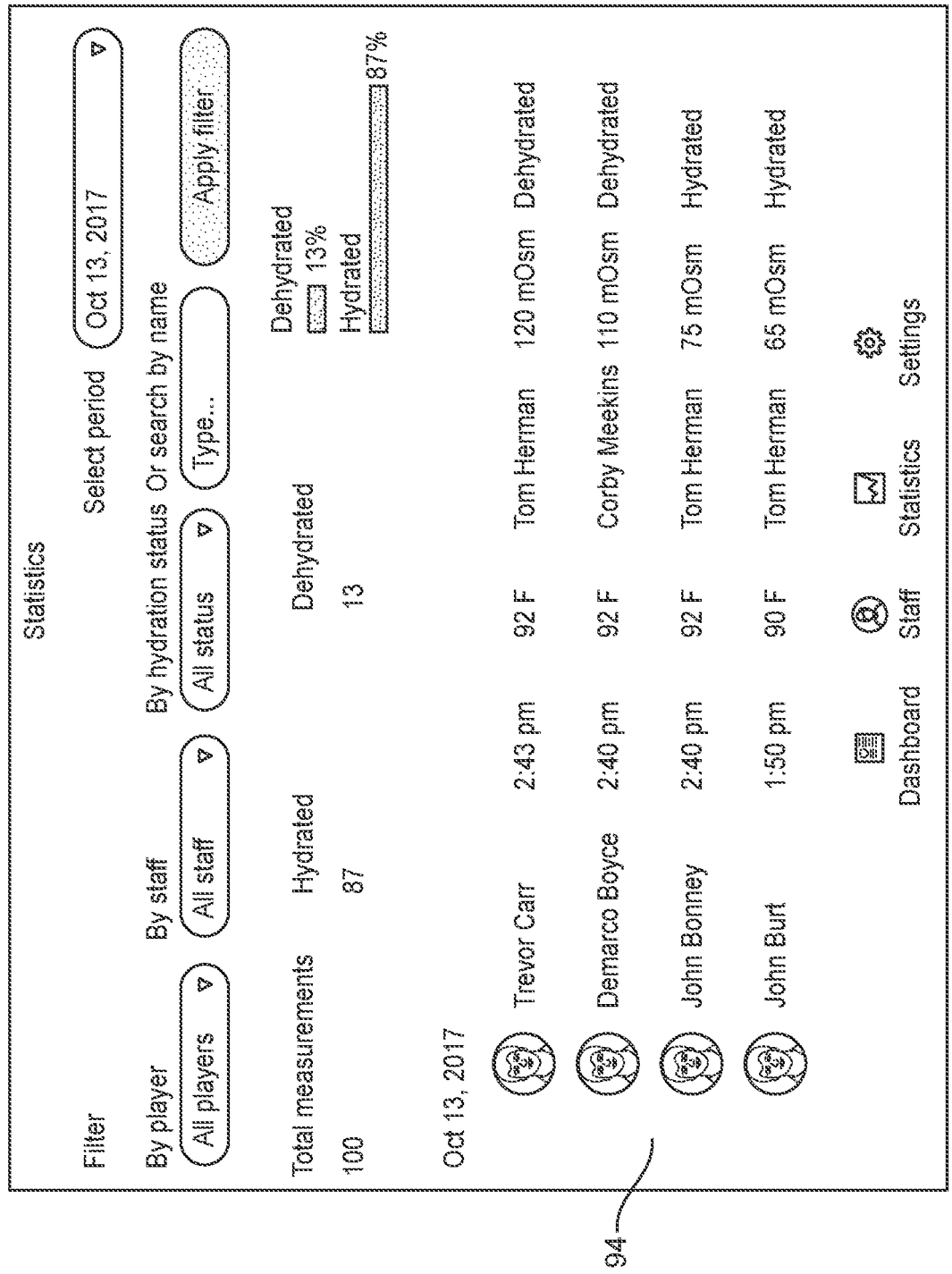
Figure 10D:
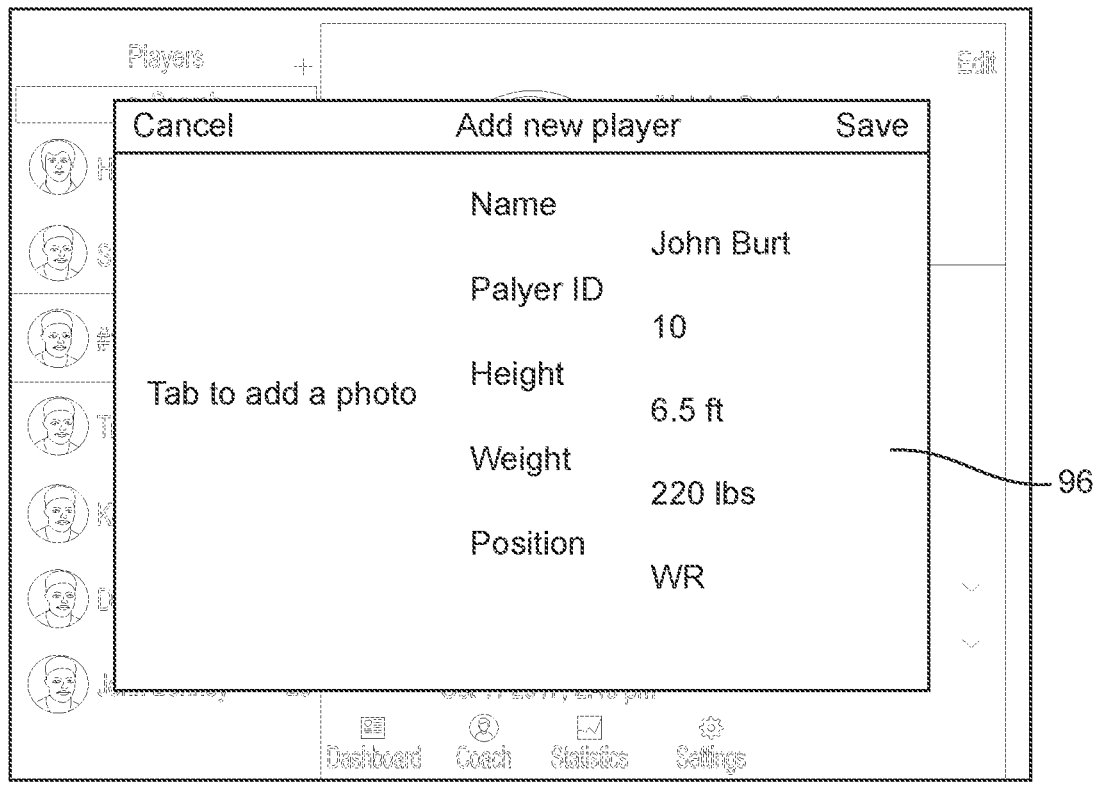
Figure 10E:
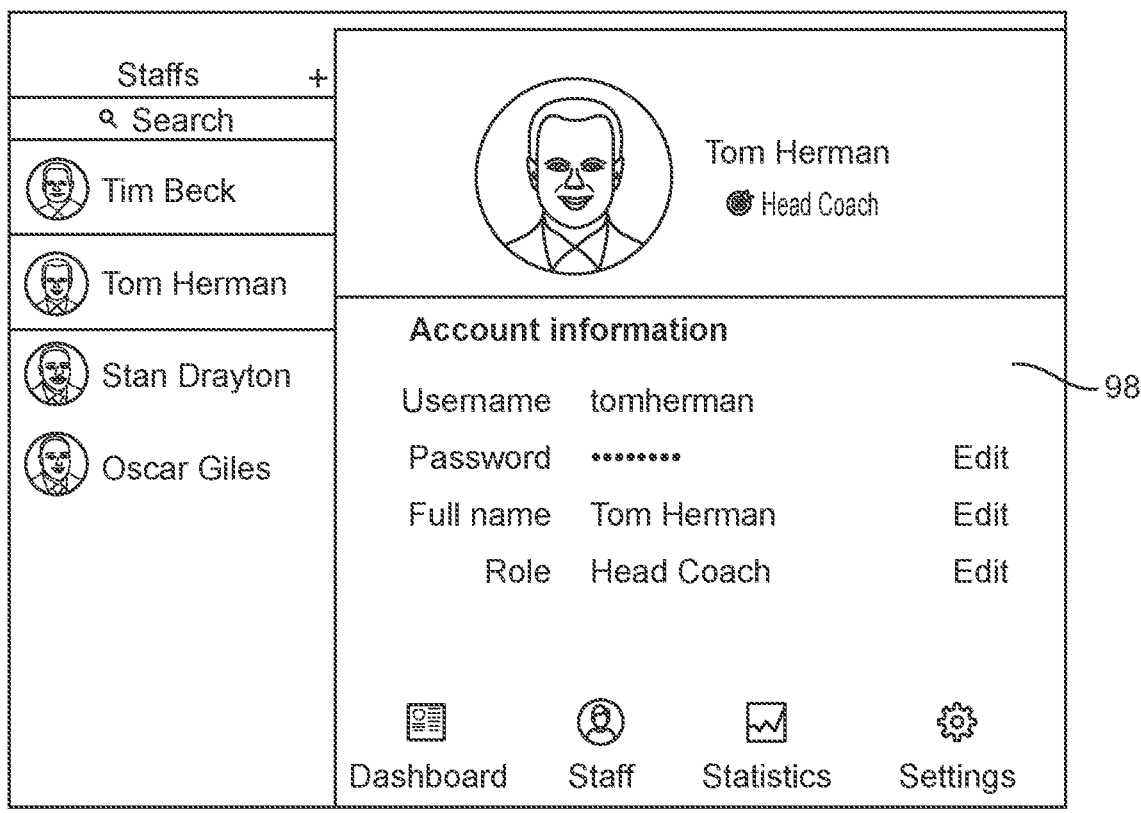
Figure 10F:
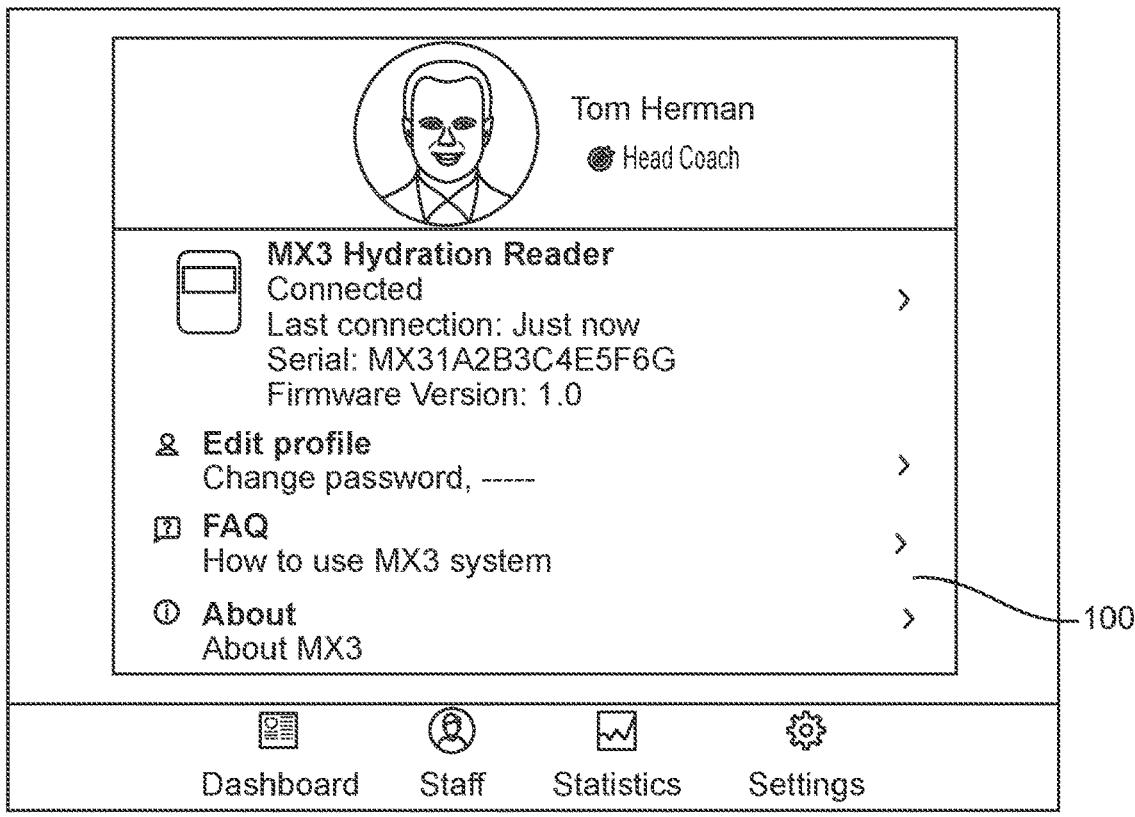
Figure 10G:
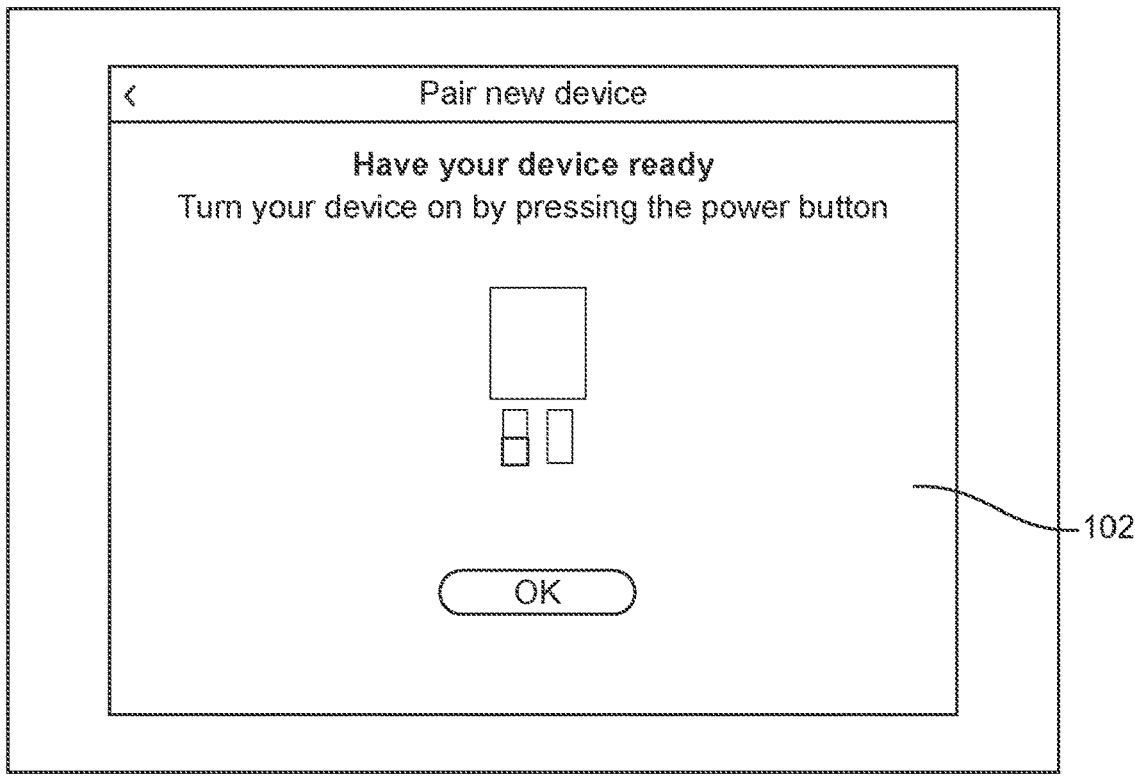

FIG. 10A shows a log-in screen 90, where a user can input a user name and password to log into computer application 16. FIG. 10B shows a player dashboard 92 screen, which provides information about a player. As illustrated on the left of the player dashboard 92, this screen allows a user to select from among a menu of multiple players. FIG. 10C shows a statistics page 94, which provides hydration statistics and information for multiple players. FIG. 10D shows an add-new-player page 96. FIG. 10E shows a staff page 98, and FIG. 10F shows a staff setting page 100 indicating a connection with a connected device. FIG. 10G is a pair-new-device page 102, for pairing a new handheld device 12 with computer application 16.

Figure 10H:
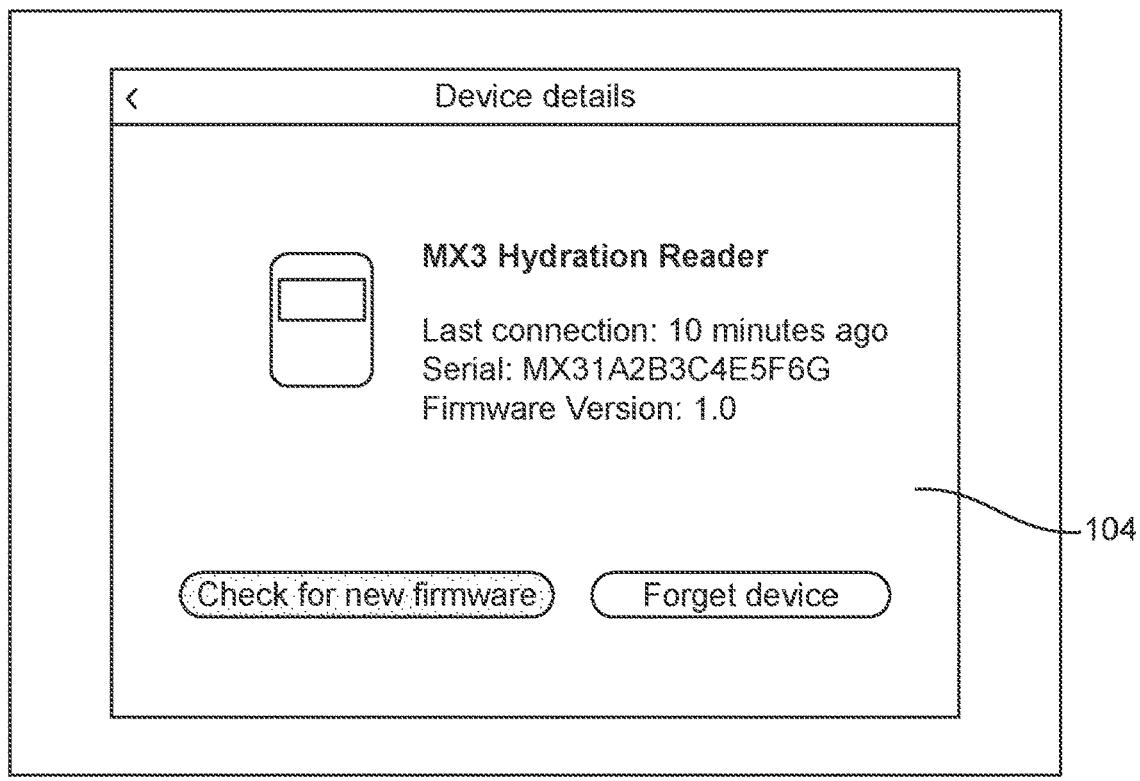
Figure 10I:
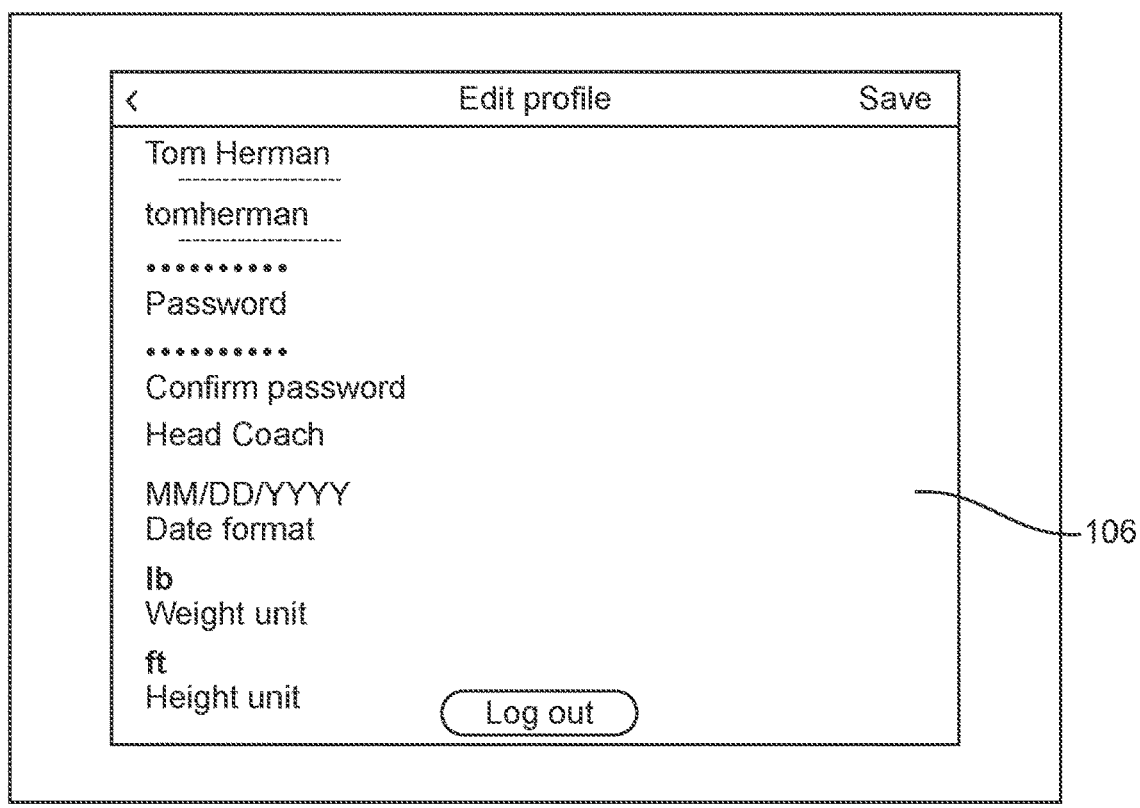
Figure 10J:
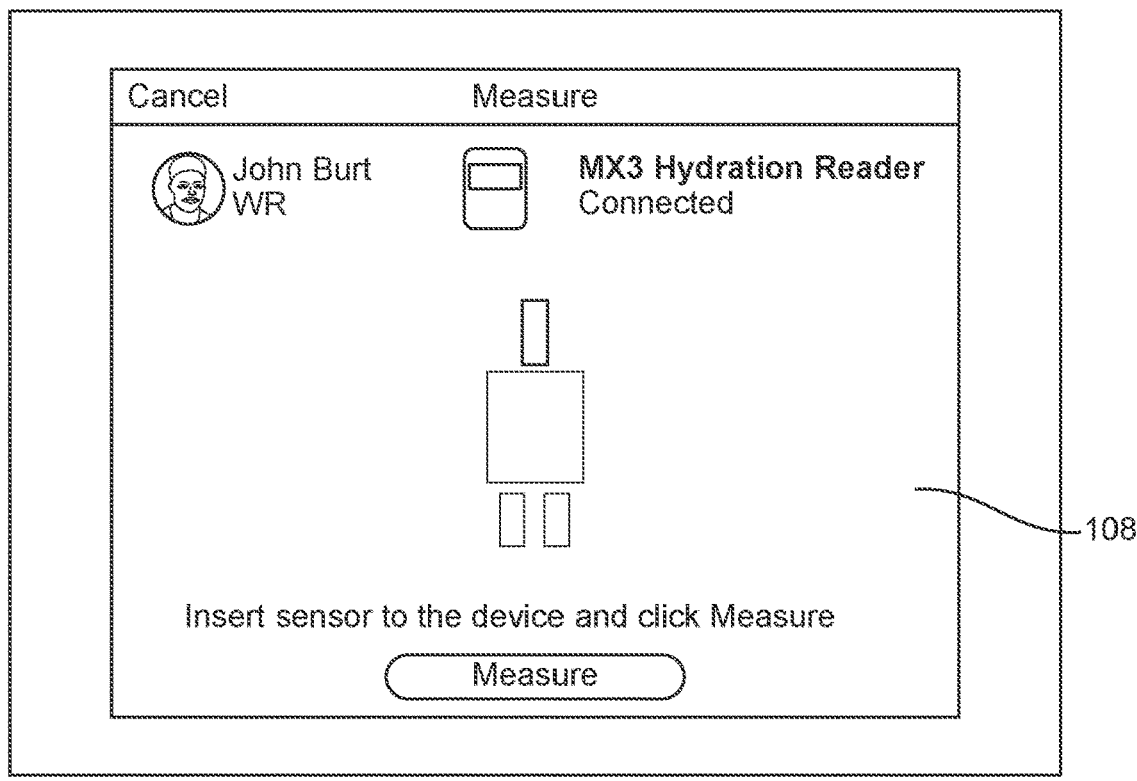
Figure 10K:
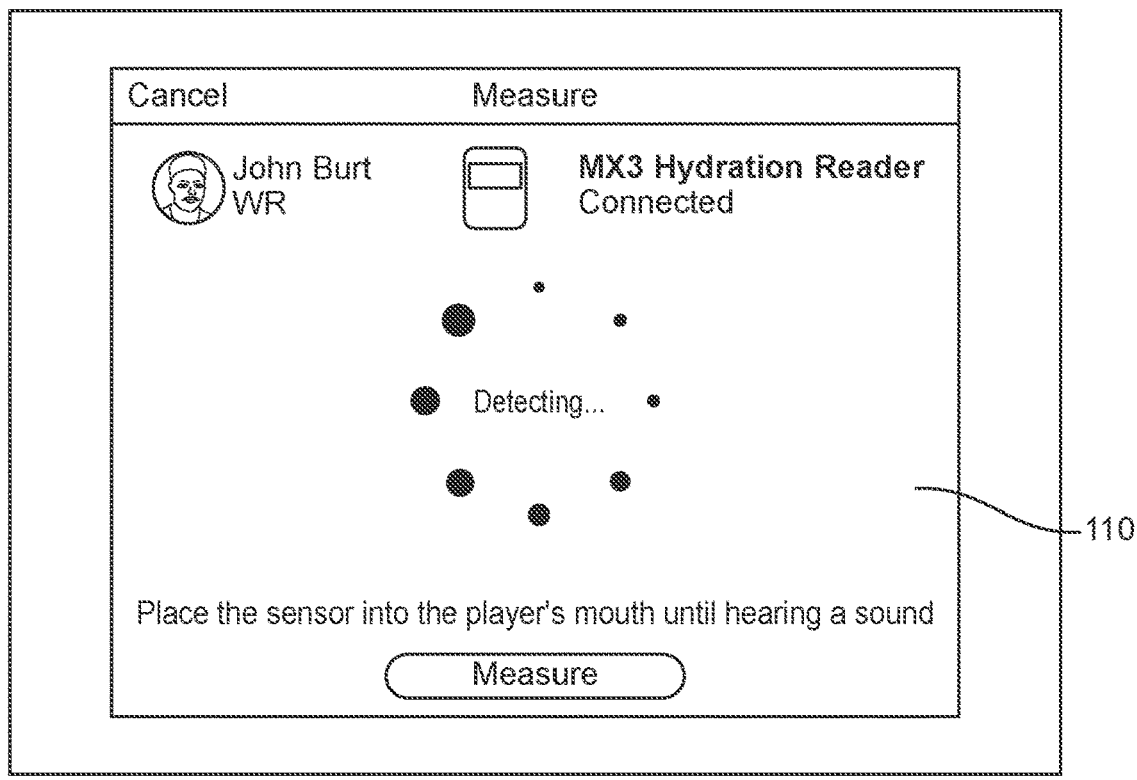
Figure 10L:
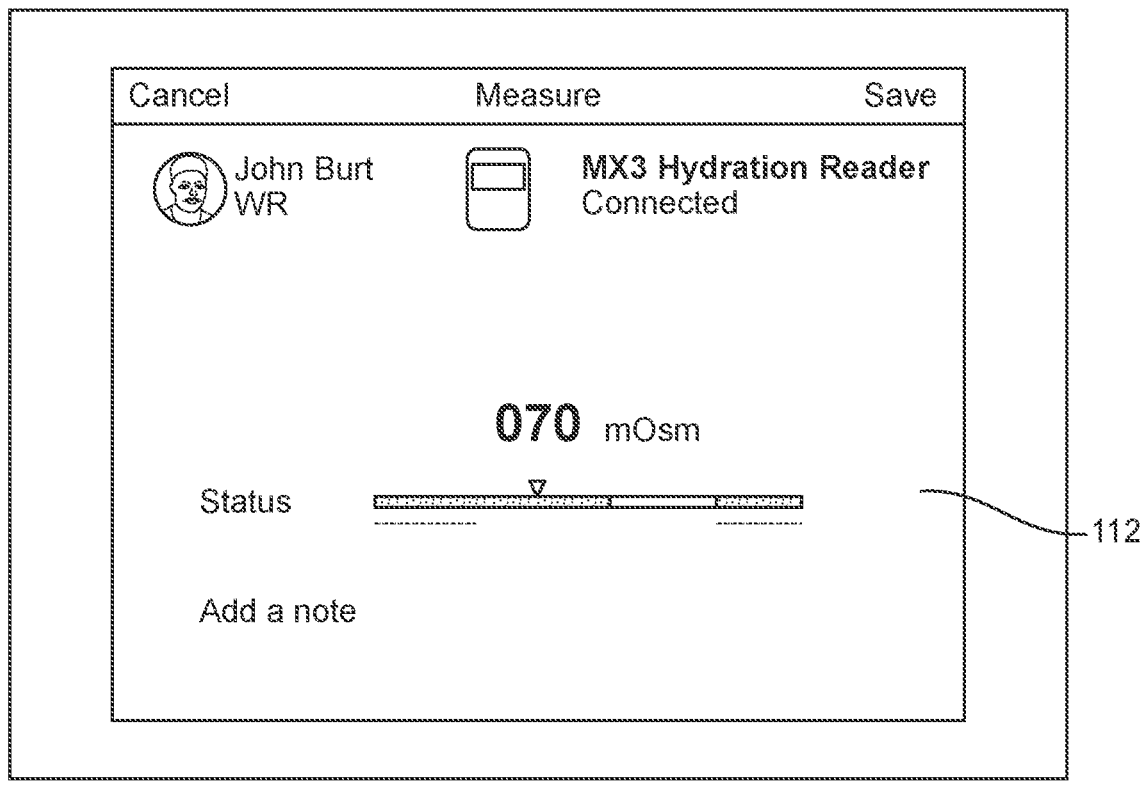

FIG. 10H is a device details page 104, where details of the paired handheld device 12 are provided. FIG. 10I is an edit profile page 106. FIG. 10J is a first measurement page 108, which tells the user to insert sensor 14 into handheld device 12 and click "Measure." FIG. 10K is a fluid detection page 110. Finally, FIG. 10L is a measurement result page 112. As mentioned above, saliva testing system 10 may provide any suitable data to a user, according to various embodiments. For example, computer application may indicate whether the test subject is hydrated or dehydrated, to what extent the subject is hydrated or dehydrated, a hydration score or rating for the subject, and/or the like. Again, the GUIs illustrated in FIGS. 10A-10L are for exemplary purposes only and are not meant to limit the scope of the application.

The above description is intended to be a complete description of one embodiment of a system and method for measuring eye tracking for one or more diagnostic purposes. It is meant to be a description of examples only and is not intended to limit the scope of the invention.

We claim:

1. A system for testing saliva to measure at least one substance or physiological parameter of a human or animal subject, the system comprising:
    a handheld saliva testing device comprising a sensor slot and a display;
    a sensor comprising:
        a first end configured for insertion into the sensor slot of the handheld saliva testing device;
        a second end configured for receiving saliva directly from the subject's mouth on the second end of the sensor while the first end of the sensor remains inserted within the handheld saliva testing device;
        at least one microfluidic channel configured to direct saliva from the second end to the first end; and
        an enzyme mesh embedded between a top layer and a bottom layer of the sensor, configured to facilitate movement of saliva along a length of the sensor; and
    a computer processor coupled with the handheld saliva testing device to process initial data from the handheld saliva testing device to provide final measurement data describing the at least one substance or physiological parameter.

2. The system of claim 1, wherein the computer processor is located separately from, and is wirelessly connectable to, the handheld saliva testing device.

3. The system of claim 1, wherein the computer processor comprises an application on a mobile computing device.

4. The system of claim 1, wherein the at least one substance or physiological parameter comprises hydration, and wherein the computer processor is configured to generate the final measurement data, including a hydration score for the subject.

5. The system of claim 1, wherein the at least one substance or physiological parameter is selected from the group consisting of hydration, lactate level, ketones, glucose, glycerides, sodium, potassium, calcium, magnesium, chlorides, phosphates, caffeine, melatonin, c-reactive protein, chemokines, cytokines, troponin, cortisol, creatinine kinase, insulin, beta hydroxyl butyrate, iron, ferritin, salivary amylase, and oxalic acid.

6. The system of claim 1, further comprising an additional computer processor embedded in the handheld saliva testing device for generating the initial data.

7. The system of claim 1, wherein the handheld saliva testing device further comprises:
    an on/off switch;
    a speaker for emitting an alert; and
    an eject button for ejecting the sensor out of the sensor slot.

8. The system of claim 1, wherein the sensor further comprises multiple electrodes applied to the bottom layer; and
    wherein the at least one microfluidic channel is located between the bottom layer and the top layer.

9. The system of claim 8, wherein the sensor further comprises an insulating layer comprising a hydrophobic, dielectric material.

10. The system of claim 8, wherein the at least one microfluidic channel comprises multiple microfluidic channels, and wherein the sensor is configured for measuring at least two substances or physiological parameters of the subject.

11. The system of claim 1, wherein the sensor further comprises an electrode at the first end.

12. The system of claim 11, wherein the electrode includes silver.

13. The system of claim 12, wherein the electrode further comprises carbon.

14. A handheld device for testing saliva to measure at least one substance or physiological parameter of a human or animal subject, the handheld device comprising:
    a housing;
    a sensor slot in the housing;
    a display on the housing;
    a computer processor housed in the housing and configured to detect a sufficient amount of saliva on a sensor inserted in the slot while saliva is received directly from the subject's mouth, and to generate initial data related to the at least one substance or parameter from the saliva; and
    a transmitter for transmitting the initial data to an additional computer processor separate from the handheld device, wherein the computer processor is configured to process the initial data from the handheld device to provide additional measurement data.

15. The device of claim 14, further comprising an eject button on the housing for ejecting a used sensor out of the sensor slot.

16. The device of claim 15, further comprising multiple buttons on the housing for controlling the handheld device.

17. The device of claim 14, wherein the transmitter is a wireless transmitter.

18. The device of claim 14, wherein the additional measurement data describes a hydration of the human or animal subject.

* * * * *

UNITED STATES PATENT AND TRADEMARK OFFICE
CERTIFICATE OF CORRECTION

PATENT NO. : 11,690,566 B2
APPLICATION NO. : 16/197530
DATED : July 4, 2023
INVENTOR(S) : Skafidas et al.

It is certified that error appears in the above-identified patent and that said Letters Patent is hereby corrected as shown below:

In the Specification

On Column 10, Line 29: Delete "FIG. 81," and insert -- FIG. 8I, --.

Signed and Sealed this
Twelfth Day of September, 2023

Katherine Kelly Vidal
*Director of the United States Patent and Trademark Office*